United States Patent
Hilpert et al.

(10) Patent No.: US 9,067,924 B2
(45) Date of Patent: Jun. 30, 2015

(54) 1,4 THIAZEPINES/SULFONES AS BACE1 AND/OR BACE2 INHIBITORS

(75) Inventors: Hans Hilpert, Muenchenstein (CH); Mark Rogers-Evans, Bottmingen (CH); Didier Rombach, Mulhouse (FR)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 129 days.

(21) Appl. No.: 13/405,398

(22) Filed: Feb. 27, 2012

(65) Prior Publication Data

US 2012/0225858 A1  Sep. 6, 2012

(30) Foreign Application Priority Data

Mar. 4, 2011 (EP) .................................. 11156976

(51) Int. Cl.
- A61K 31/554 (2006.01)
- C07D 417/10 (2006.01)
- C07D 513/04 (2006.01)
- C07D 417/12 (2006.01)

(52) U.S. Cl.
CPC ............ C07D 417/12 (2013.01); C07D 513/04 (2013.01); A61K 31/554 (2013.01)

(58) Field of Classification Search
CPC ... A61K 31/554; C07D 417/12; C07D 513/04
USPC .............. 514/211.1, 211.15, 211.01; 540/544, 540/552
See application file for complete search history.

(56) References Cited

FOREIGN PATENT DOCUMENTS

| WO | 2010/128058 | 11/2010 |
| WO | 2011009943 | 1/2011 |
| WO | 2011/020806 | 2/2011 |

OTHER PUBLICATIONS

"International Search Report—PCT/EP2012/053298—mailed Apr. 12, 2012".
Roberds et al., Hum. Mol. Genet. 10(12):1317-1324 (2001).
Selkoe et al., "Annual Review Cell Biology" 10:373-403 (1994).
Hardy et al., "Science" 297 (5580):353-356 (2002).
Prentki et al., J. Clin. Investig. 116(7):1802-1812 (2006).
Zimmet et al., Nature 414:782-787 (2001).
McConlogue et al., "J. Biol. Chem." 282(36):26326-26334 (2007).
Baggio et al., Annu. Rev. Med. 57:265-281 (2006).
Kuhn et al., "J. Biol. Chem." 282(16):11982-11995 (2007).
Hussain et al., "Molecular & Cellular Neurosciences" 16:609-619 (2000).
Fukui et al., Cell Metab. 2:373-384 (2005).
Akpinar et al., Cell Metab. 2:385-397 (2005).
Finzi et al., "Ultrastruct. Pathol." 32(6):246-251 (2008).
Luo et al., "Nature Neuroscience" 3:231-232 (2001).
Vassar et al., "Science" ((5440)), 286:735-741 (1999).
Wild et al., "Diabetes Care" 27:1047-1053 (2004).
The Chinese Office Action, issued on Oct. 22, 2014, in the corresponding Chinese application No. 201280011646.9.

*Primary Examiner* — Brenda Coleman

(57) ABSTRACT

The present invention relates to 1,4 Thiazepines/Sulfones of formula I

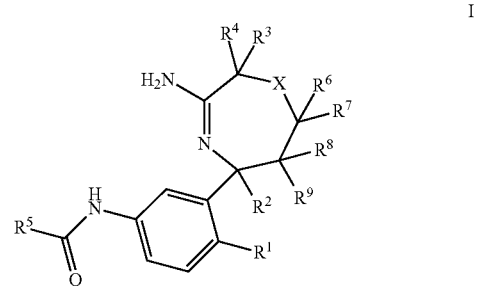

having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes.

23 Claims, No Drawings

1,4 THIAZEPINES/SULFONES AS BACE1 AND/OR BACE2 INHIBITORS

PRIORITY TO RELATED APPLICATION(S)

This application claims the benefit of European Patent Application No. 11156976.0, field Mar. 4, 2011, which is hereby incorporated by reference in its entirety.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297 (5580:353-6, Selkoe, Cell biology of the amyloid beta-protein precursor and the mechanism of Alzheimer's disease, *Annu Rev Cell Biol*. 1994; 10:373-403). Both pathologies are also commonly observed in patients with Down's syndrome (trisomy 21), which also develop Aβ-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci*. 2001 March; 4(3):231-2, Roberds et al., BACE knockout mice are healthy despite lacking the primary beta-secretase activity in brain: implications for Alzheimer's disease therapeutics, *Hum Mol Genet*. 2001 Jun. 1; 10(12): 1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem*. 2007 Sep. 7; 282(36):26326). It is thus presumed that inhibitors of BACE1 activity can be useful agents for therapeutic intervention in Alzheimer's disease (AD).

Type 2 diabetes (T2D) is caused by insulin resistance and inadequate insulin secretion from pancreatic β-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, KGMM Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu. Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

FIELD OF THE INVENTION

The present invention relates to 1,4-Thiazepines and 1,4-Sulfones having BACE1 and/or BACE2 inhibitory properties, their manufacture, pharmaceutical compositions containing them and their use as therapeutically active substances.

SUMMARY OF THE INVENTION

The present invention provides novel compounds of formula I, their manufacture, pharmaceutical compositions containing a compound of the invention and their production as well as the use of compounds of formula I in the control or prevention of illnesses such as Alzheimer's disease and type 2 diabetes.

The present invention provides a compounds of formula I,

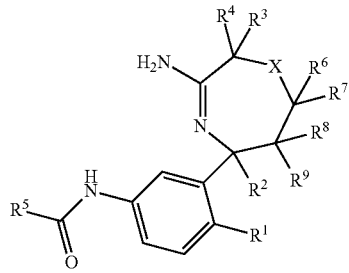

wherein the substituents and variables are as described below and in the claims, or a pharmaceutically acceptable salt thereof.

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits or Alzheimer's disease. And/or the present compounds have BACE2 inhibitory activity and can therefore be used in the therapeutic and/or prophylactic treatment of diseases and disorders such as type 2 diabetes and other metabolic disorders.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1 and/or BACE2 activity, such as Alzheimer's disease and type 2 diabetes. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which can be linear or branched, with single or multiple branching, wherein the alkyl group in general contains 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular "$C_{1-6}$-alkyl" are groups with 1 to 5 carbon atoms. Specific examples are methyl, ethyl and t-butyl—most specifically methyl.

The term "halogen-$C_{1-6}$-alkyl", alone or in combination with other groups, refers to $C_{1-6}$-alkyl as defined herein, which is substituted by one or multiple halogen, preferably 1-5 halogen, more preferably 1-3 halogen, most preferably 1 halogen or 3 halogen. Particular halogen is fluoro. Particular "halogen-$C_{1-6}$-alkyl" is fluoro-$C_{1-6}$-alkyl. Examples are difluoromethyl, chloromethyl, fluoromethyl and the like. Specific are trifluoromethyl and difluoromethyl.

The term "halogen", alone or in combination with other groups, denotes chloro (Cl), iodo (I), fluoro (F) and bromo (Br). Particular "halogen" is Cl and F. Specific is F.

The term "heteroaryl", alone or in combination with other groups, refers to an aromatic group having a single 4 to 8 membered ring or multiple condensed rings containing 6 to 14, in particular 6 to 10, ring atoms and containing 1, 2 or 3 heteroatoms individually selected from N, O and S, in particular N and O, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" are pyridinyl and 2H-pyrazolyl. Specific examples are pyridine-2-yl and 2H-pyrazole-3-yl.

The term "$C_{1-6}$-alkoxy", alone or in combination with other groups, stands for an —O—$C_{1-6}$-alkyl radical which can be linear or branched, with single or multiple branching, wherein the alkyl group contains 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. Specific examples are methoxy and ethyoxy.

The term "heterocyclyl", alone or in combination with other groups, refers to a 4 to 8 membered ring containing 1, 2 or 3 ring heteroatoms individually selected from N, O and S. 1 or 2 ring heteroatoms are preferred. Particular are 4 to 6 membered "heterocyclyl", more particular 5 to 6 membered "heterocyclyl", each containing 1 or 2 ring heteroatoms selected from N, O and S, in particular O. Specific is a 5-membered heterocycle containing a single O. Examples of "heterocyclyl" include azepanyl, azetidyl, diazepanyl, morpholinyl, oxazepanyl, oxazolidyl, oxetanyl, piperazinyl, piperidyl, pyrrolidinyl, tetrahydrofuryl, tetrahydropyridyl, tetrahydropyryl, tetrahydrothienyl, thiazolidyl, thiomorpholinyl and the like. A specific example is tetrahydrofuryl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Preferred are formic acid, trifluoroacetic acid and hydrochloric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "amino-protecting group" denotes groups intended to protect an amino group and includes benzyl, benzyloxycarbonyl (carbobenzyloxy, CBZ), 9-Fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups. Particular amino-protecting groups are tert-butoxycarbonyl group, a bis(dimethoxyphenyl)-phenylmethyl and dimethoxytrityl.

The term "leaving group" denotes the group with the meaning conventionally associated with it in synthetic organic chemistry, i.e., an atom or group displaceable under substitution reaction conditions. Examples of leaving groups include halogen, in particular bromo, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, and acyloxy.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure.

The invention also provides pharmaceutical compositions, methods of using, and methods of preparing the aforementioned compounds.

All separate embodiments can be combined.

A certain embodiments is a compound of formula I,

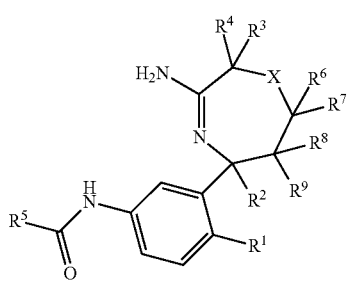

wherein
$R^1$ is selected from the group consisting of
 hydrogen,
 halogen, and
 $C_{1-6}$-alkyl;
$R^2$ is selected from the group consisting of
 hydrogen,
 $C_{1-6}$-alkyl, and
 halogen-$C_{1-6}$-alkyl;
$R^3$ is selected from the group consisting of
 hydrogen and
 $C_{1-6}$-alkyl;
$R^4$ is selected from the group consisting of
 hydrogen and
 $C_{1-6}$-alkyl;
$R^5$ is heteroaryl unsubstituted or substituted by one or two substituents individually selected from the group consisting of
 $C_{1-6}$-alkyl,
 halogen,
 $C_{1-6}$-alkoxy, and
 halogen-$C_{1-6}$-alkyl,
$R^6$ is hydrogen;
$R^7$ is hydrogen;
$R^8$ is hydrogen;
$R^9$ is hydrogen;
or $R^6$ and $R^8$ form together a 5-6 membered heterocyclyl; and
X is selected from the group consisting of
 —S and
 —SO$_2$;
or pharmaceutically acceptable salts thereof.

A certain embodiment of the invention is a compound of formula I',

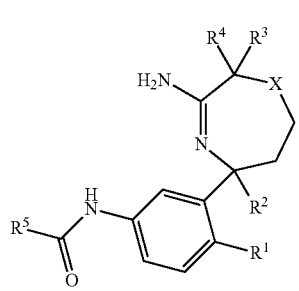

wherein
$R^1$ is selected from the group consisting of
 hydrogen,
 halogen, and
 $C_{1-6}$-alkyl;
$R^2$ is selected from the group consisting of
 hydrogen,
 $C_{1-6}$-alkyl, and
 halogen-$C_{1-6}$-alkyl;
$R^3$ is selected from the group consisting of
 hydrogen and
 $C_{1-6}$-alkyl;
$R^4$ is selected from the group consisting of
 hydrogen and
 $C_{1-6}$-alkyl;
$R^5$ is heteroaryl unsubstituted or substituted by one or two substituents individually selected from the group consisting of
 $C_{1-6}$-alkyl,
 halogen,
 $C_{1-6}$-alkoxy, and
 halogen-$C_{1-6}$-alkyl; and
X is selected from the group consisting of
 —S and
 —SO$_2$;
or pharmaceutically acceptable salts thereof.

A certain embodiment of the invention provides a compound of formula I'a as described herein,

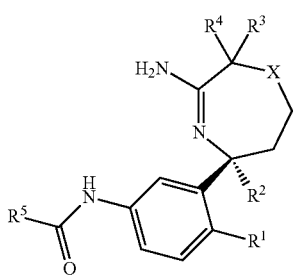

wherein
R¹ is selected from the group consisting of
  hydrogen,
  halogen, and
  $C_{1-6}$-alkyl;
R² is selected from the group consisting of
  hydrogen,
  $C_{1-6}$-alkyl, and
  halogen-$C_{1-6}$-alkyl;
R³ is selected from the group consisting of
  hydrogen, and
  $C_{1-6}$-alkyl;
R⁴ is selected from the group consisting of
  hydrogen and
  $C_{1-6}$-alkyl;
R⁵ is heteroaryl unsubstituted or substituted by one or two substituents individually selected from the group consisting of
  $C_{1-6}$-alkyl,
  halogen,
  $C_{1-6}$-alkoxy, and
  halogen-$C_{1-6}$-alkyl; and
X is selected from the group consisting of
  —S and
  —$SO_2$;
or pharmaceutically acceptable salts thereof.

A certain embodiment of the invention provides a compound of formula I as described herein, wherein R¹ is halogen.

A certain embodiment of the invention provides a compound of formula I as described herein, wherein R¹ is F.

A certain embodiment of the invention provides a compound of formula I as described herein, wherein R² is $C_{1-6}$-alkyl.

A certain embodiment of the invention provides a compound of formula I as described herein, wherein R² is Me.

A certain embodiment of the invention provides a compound of formula I as described herein, wherein R² is halogen-$C_{1-6}$-alkyl.

A certain embodiment of the invention provides a compound of formula I as described herein, wherein R² is —$CHF_2$.

A certain embodiment of the invention provides a compound of formula I as described herein, wherein R³ is $C_{1-6}$-alkyl.

A certain embodiment of the invention provides a compound of formula I as described herein, wherein R³ is Me.

A certain embodiment of the invention provides a compound of formula I as described herein, wherein R⁴ is $C_{1-6}$-alkyl.

A certain embodiment of the invention provides a compound of formula I as described herein, wherein R⁴ is Me.

A certain embodiment of the invention provides a compound of formula I as described herein, wherein R⁴ is hydrogen.

A certain embodiment of the invention provides a compound of formula I as described herein, wherein R³ is Me.

A certain embodiment of the invention provides a compound of formula I as described herein, wherein R⁶ is hydrogen.

A certain embodiment of the invention provides a compound of formula I as described herein, wherein R⁷ is hydrogen.

A certain embodiment of the invention provides a compound of formula I as described herein, wherein R⁸ is hydrogen.

A certain embodiment of the invention provides a compound of formula I as described herein, wherein R⁹ is hydrogen.

A certain embodiment of the invention provides a compound of formula I as described herein, wherein R⁶ and R⁸ form together a 5-6 membered heterocyclyl.

A certain embodiment of the invention provides a compound of formula I as described herein, wherein R⁶ and R⁸ form tetrahydrofuryl.

A certain embodiment of the invention provides a compound of formula I as described herein, wherein X is $SO_2$, R¹ is halogen, R² is $C_{1-6}$-alkyl, R³ is hydrogen and R⁴ is hydrogen.

A certain embodiment of the invention provides a compound of formula I as described herein, wherein X is $SO_2$, R¹ is F, R² is Me, R³ is hydrogen and R⁴ is hydrogen.

A certain embodiment of the invention provides a compound of formula I as described herein, wherein X is $SO_2$, R¹ is halogen, R² is $C_{1-6}$-alkyl, R³ is hydrogen and R⁴ is $C_{1-6}$-alkyl.

A certain embodiment of the invention provides a compound of formula I as described herein, wherein X is $SO_2$, R¹ is F, R² is Me, R³ is hydrogen and R⁴ is Me.

A certain embodiment of the invention provides a compound of formula I as described herein, wherein X is $SO_2$, R⁵ is heteroaryl substituted by one halogen selected from chloro and fluoro.

A certain embodiment of the invention provides a compound of formula I as described herein, wherein R¹ is halogen, R² is $C_{1-6}$-alkyl, R³ is hydrogen and R⁴ is hydrogen.

A certain embodiment of the invention provides a compound of formula I as described herein, wherein R¹ is F, R² is Me, R³ is hydrogen and R⁴ is hydrogen.

A certain embodiment of the invention provides a compound of formula I as described herein, wherein R¹ is halogen, R² is $C_{1-6}$-alkyl, R³ is hydrogen and R⁴ is $C_{1-6}$-alkyl.

A certain embodiment of the invention provides a compound of formula I as described herein, wherein R¹ is F, R² is Me, R³ is hydrogen and R⁴ is Me.

A certain embodiment of the invention provides a compound of formula I as described herein, wherein R⁵ is heteroaryl substituted by one halogen selected from chloro and fluoro.

A certain embodiment of the invention provides a compound of formula I as described herein, wherein R⁵ is selected from
i) chloro-pyridinyl,
ii) fluoro-pyridinyl, and
iii) 2H-pyrazolyl.

A certain embodiment of the invention provides a compound of formula I as described herein wherein R⁵ is chloro-pyridinyl.

A certain embodiment of the invention provides a compound of formula I as described herein wherein $R^5$ is fluoropyridinyl.

A certain embodiment of the invention provides a compound of formula I as described herein wherein $R^5$ is 2H-pyrazole-3-yl.

A certain embodiment of the invention provides a compound of formula I as described herein, wherein $R^5$ is 5-chloro-pyridine-2-yl or 5-fluoro-pyridine-2-yl.

A certain embodiment of the invention provides a compound of formula I as described herein, wherein $R^5$ is 5-chloro-pyridine-2-yl.

A certain embodiment of the invention provides a compound of formula I as described herein, wherein $R^5$ is 5-fluoro-pyridine-2-yl.

A certain embodiment of the invention provides a compound of formula I as described herein, wherein X is S.

A certain embodiment of the invention provides a compound of formula I as described herein, wherein X is —$SO_2$.

A certain embodiment of the invention provides a compound of formula I as described herein, selected from the group consisting of 5-Chloro-pyridine-2-carboxylic acid [3-((S)-3-amino-5-methyl-2,5,6,7-tetrahydro-[1,4]thiazepin-5-yl)-4-fluoro-phenyl]-amide, 4-Chloro-2H-pyrazole-3-carboxylic acid [3-((S)-3-amino-2,2,5-trimethyl-1,1-dioxo-2,5,6,7-tetrahydro-1H-1$\lambda^6$-[1,4]thiazepin-5-yl)-4-fluoro-phenyl]-amide, 4-Chloro-2H-pyrazole-3-carboxylic acid [3-((S)-3-amino-2,5-dimethyl-1,1-dioxo-2,5,6,7-tetrahydro-1H-1$\lambda^6$-[1,4]thiazepin-5-yl)-4-fluoro-phenyl]-amide, 5-Chloro-pyridine-2-carboxylic acid [3-((S)-3-amino-2,5-dimethyl-2,5,6,7-tetrahydro-[1,4]thiazepin-5-yl)-4-fluoro-phenyl]-amide, 5-Chloro-pyridine-2-carboxylic acid [3-((S)-3-amino-2,5-dimethyl-1,1-dioxo-2,5,6,7-tetrahydro-1H-1$\lambda^6$-[1,4]thiazepin-5-yl)-4-fluoro-phenyl]-amide, 5-Chloro-pyridine-2-carboxylic acid [3-((S)-3-amino-5-methyl-1,1-dioxo-2,5,6,7-tetrahydro-1H-1$\lambda^6$-[1,4]thiazepin-5-yl)-4-fluoro-phenyl]-amide, 5-Fluoro-pyridine-2-carboxylic acid [3-((S)-3-amino-2,2,5-trimethyl-1,1-dioxo-2,5,6,7-tetrahydro-1H-1$\lambda^6$-[1,4]thiazepin-5-yl)-4-fluoro-phenyl]-amide, 5-Fluoro-pyridine-2-carboxylic acid [3-((S)-3-amino-2,5-dimethyl-2,5,6,7-tetrahydro-[1,4]thiazepin-5-yl)-4-fluoro-phenyl]-amide, 5-Fluoro-pyridine-2-carboxylic acid [3-((S)-3-amino-2,5-dimethyl-1,1-dioxo-2,5,6,7-tetrahydro-1H-1$\lambda^6$-[1,4]thiazepin-5-yl)-4-fluoro-phenyl]-amide, 5-Fluoro-pyridine-2-carboxylic acid [3-((S)-3-amino-5-methyl-1,1-dioxo-2,5,6,7-tetrahydro-1H-1$\lambda^6$-[1,4]thiazepin-5-yl)-4-fluoro-phenyl]-amide, 5-Fluoro-pyridine-2-carboxylic acid [3-((S)-3-amino-5-methyl-2,5,6,7-tetrahydro-[1,4]thiazepin-5-yl)-4-fluoro-phenyl]-amide, 5-Cyano-pyridine-2-carboxylic acid [3-((S)-3-amino-2,2,5-trimethyl-1,1-dioxo-2,5,6,7-tetrahydro-1H-1$\lambda$6-[1,4]thiazepin-5-yl)-4-fluoro-phenyl]-amide, 5-Cyano-pyridine-2-carboxylic acid [3-((S)-3-amino-5-difluoromethyl-1,1-dioxo-2,5,6,7-tetrahydro-1H-1$\lambda$6-[1,4]thiazepin-5-yl)-4-fluoro-phenyl]-amide, and 5-Cyano-pyridine-2-carboxylic acid [3-((3aR,8S,8aS)-rel-6-amino-8-methyl-4,4-dioxo-3,3a,4,5,8,8a-hexahydro-1H-2-oxa-4$\lambda$6-thia-7-aza-azulen-8-yl)-4-fluoro-phenyl]-amide, or a pharmaceutical acceptable salt thereof.

A certain embodiment of the invention provides a compound of formula I as described herein, selected from the group consisting of 5-Chloro-pyridine-2-carboxylic acid [3-((S)-3-amino-5-methyl-2,5,6,7-tetrahydro-[1,4]thiazepin-5-yl)-4-fluoro-phenyl]-amide, 4-Chloro-2H-pyrazole-3-carboxylic acid [3-((S)-3-amino-2,2,5-trimethyl-1,1-dioxo-2,5,6,7-tetrahydro-1H-1$\lambda^6$-[1,4]thiazepin-5-yl)-4-fluoro-phenyl]-amide, 4-Chloro-2H-pyrazole-3-carboxylic acid [3-((S)-3-amino-2,5-dimethyl-1,1-dioxo-2,5,6,7-tetrahydro-1H-1$\lambda^6$-[1,4]thiazepin-5-yl)-4-fluoro-phenyl]amide, 5-Chloro-pyridine-2-carboxylic acid [3-((S)-3-amino-2,5-dimethyl-2,5,6,7-tetrahydro-[1,4]thiazepin-5-yl)-4-fluoro-phenyl]-amide, 5-Chloro-pyridine-2-carboxylic acid [3-((S)-3-amino-2,5-dimethyl-1,1-dioxo-2,5,6,7-tetrahydro-1H-1$\lambda^6$-[1,4]thiazepin-5-yl)-4-fluoro-phenyl]-amide, 5-Chloro-pyridine-2-carboxylic acid [3-((S)-3-amino-5-methyl-1,1-dioxo-2,5,6,7-tetrahydro-1H-1$\lambda^6$-[1,4]thiazepin-5-yl)-4-fluoro-phenyl]-amide, 5-Fluoro-pyridine-2-carboxylic acid [3-((S)-3-amino-2,2,5-trimethyl-1,1-dioxo-2,5,6,7-tetrahydro-1H-1$\lambda^6$-[1,4]thiazepin-5-yl)-4-fluoro-phenyl]amide, 5-Fluoro-pyridine-2-carboxylic acid [3-((S)-3-amino-2,5-dimethyl-2,5,6,7-tetrahydro-[1,4]thiazepin-5-yl)-4-fluoro-phenyl]-amide, 5-Fluoro-pyridine-2-carboxylic acid [3-((S)-3-amino-2,5-dimethyl-1,1-dioxo-2,5,6,7-tetrahydro-1H-1$\lambda^6$-[1,4]thiazepin-5-yl)-4-fluoro-phenyl]-amide, 5-Fluoro-pyridine-2-carboxylic acid [3-((S)-3-amino-5-methyl-1,1-dioxo-2,5,6,7-tetrahydro-1H-1$\lambda^6$-[1,4]thiazepin-5-yl)-4-fluoro-phenyl]-amide, and 5-Fluoro-pyridine-2-carboxylic acid [3-((S)-3-amino-5-methyl-2,5,6,7-tetrahydro-[1,4]thiazepin-5-yl)-4-fluoro-phenyl]-amide, or a pharmaceutical acceptable salt thereof.

A certain embodiment of the invention provides a compound of formula I as described herein, selected from the group consisting of 5-Chloro-pyridine-2-carboxylic acid [3-((S)-3-amino-5-methyl-1,1-dioxo-2,5,6,7-tetrahydro-1H-1$\lambda^6$-[1,4]thiazepin-5-yl)-4-fluoro-phenyl]-amide, 5-Chloro-pyridine-2-carboxylic acid [3-((S)-3-amino-2,5-dimethyl-1,1-dioxo-2,5,6,7-tetrahydro-1H-1$\lambda^6$-[1,4]thiazepin-5-yl)-4-fluoro-phenyl]-amide, and 5-Fluoro-pyridine-2-carboxylic acid [3-((S)-3-amino-5-methyl-1,1-dioxo-2,5,6,7-tetrahydro-1H-1$\lambda^6$-[1,4]thiazepin-5-yl)-4-fluoro-phenyl]-amide.

A certain embodiment of the invention provides a compound of formula I as described herein, which is 5-Chloro-pyridine-2-carboxylic acid [3-((S)-3-amino-5-methyl-1,1-dioxo-2,5,6,7-tetrahydro-1H-1$\lambda^6$-[1,4]thiazepin-5-yl)-4-fluoro-phenyl]-amide.

A certain embodiment of the invention provides a compound of formula I as described herein, which is 5-Chloro-pyridine-2-carboxylic acid [3-((S)-3-amino-2,5-dimethyl-1,1-dioxo-2,5,6,7-tetrahydro-1H-1$\lambda^6$-[1,4]thiazepin-5-yl)-4-fluoro-phenyl]-amide.

A certain embodiment of the invention provides a compound of formula I as described herein, which is 5-Fluoro-pyridine-2-carboxylic acid [3-((S)-3-amino-5-methyl-1,1-dioxo-2,5,6,7-tetrahydro-1H-1$\lambda^6$-[1,4]thiazepin-5-yl)-4-fluoro-phenyl]-amide.

A certain embodiment of the invention provides a process for preparing a compound of formula I as defined herein, which process comprises reacting a compound of formula A9 to a compound of formula A10,

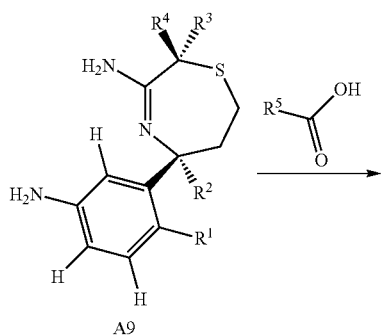

A9

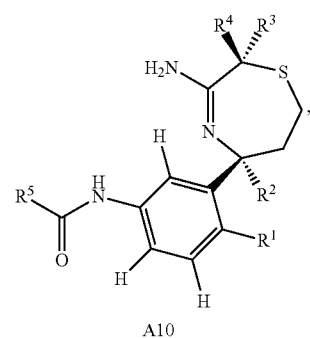

A10 optionally, a compound of formula A10 can react further with a peroxide to a compound of formula A11,

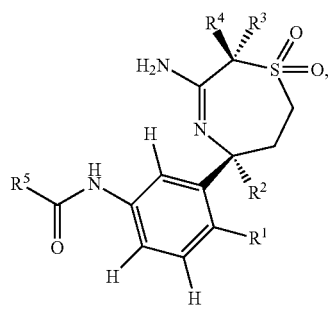

A11 wherein $R^1$, $R^2$, $R^3$, $R^4$, $R^5$ are as defined herein.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 and/or BACE2 activity.

A certain embodiment of the invention provides a compound of formula I as described herein for the use as inhibitor of BACE1 activity.

A certain embodiment of the invention provides a compound of formula I as described herein for the use as inhibitor of BACE2 activity.

A certain embodiment of the invention provides a compound of formula I as described herein for the use as inhibitor of BACE1 and BACE2 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of diabetes or type 2 diabetes.

A certain embodiment of the invention provides a compound of formula I as described herein for the use as therapeutically active substance for the therapeutic and/or prophylactic treatment of diabetes.

A certain embodiment of the invention provides a compound of formula I as described herein for the use as therapeutically active substance for the therapeutic and/or prophylactic treatment of Alzheimer's disease, diabetes or type 2 diabetes.

A certain embodiment of the invention provides a pharmaceutical composition containing a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 and/or BACE2 activity.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the use in inhibition of BACE2 activity.

A certain embodiment of the invention provides the use of a compound of formula I as described herein for the manufacture of a medicament for the use in inhibition of BACE1 and BACE2 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of Alzheimer's disease, diabetes or type 2 diabetes.

A certain embodiment of the invention provides a compound of formula I as described herein for the use in inhibition of BACE1 and/or BACE2 activity.

A certain embodiment of the invention provides a compound of formula I as described herein for the use in inhibition of BACE1 activity.

A certain embodiment of the invention provides a compound of formula I as described herein for the use in inhibition of BACE2 activity.

A certain embodiment of the invention provides a compound of formula I as described herein for the use in inhibition of BACE1 and BACE2 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of diabetes or type 2 diabetes.

A certain embodiment of the invention provides a compound of formula I as described herein for the use in the therapeutic and/or prophylactic treatment of diabetes.

A certain embodiment of the invention provides a compound of formula I as described herein for the use in the therapeutic and/or prophylactic treatment of Alzheimer's disease, diabetes or type 2 diabetes.

A certain embodiment of the invention provides a method for the use in inhibition of BACE1 and/or BACE2 activity, particularly for the therapeutic and/or prophylactic treatment of diseases and disorders characterized by elevated β-amyloid levels and/or β-amyloid oligomers and/or β-amyloid plaques and further deposits, Alzheimer's disease, diabetes or type 2 diabetes, which method comprises administering compound of formula I as described herein to a human being or animal.

A certain embodiment of the invention provides a method for the use in the therapeutic and/or prophylactic treatment of Alzheimer's disease, diabetes or type 2 diabetes, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I or I' can exist in tautomeric forms, e.g. I' can exist in the following tautomeric forms:

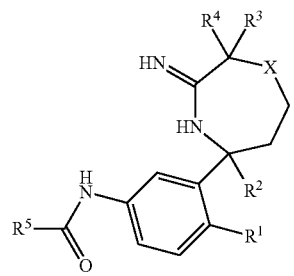
I'd

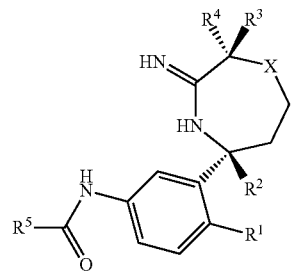
I'd-1

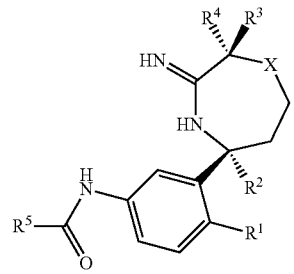
I'd-2

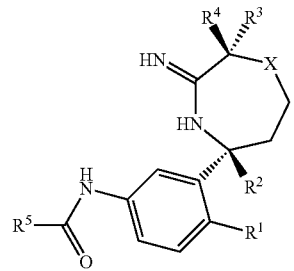
I'd-3

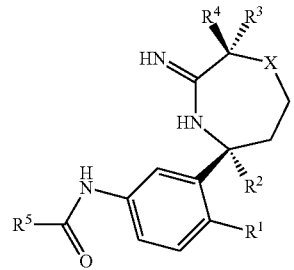
I'd-4

All tautomeric forms are encompassed in the present invention.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric center of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Preferred examples of isomers of a compound of formula I' is a compound of formula I' a or a compound of formula I' b, in particular I' b, wherein the residues have the meaning as described in any of the embodiments.

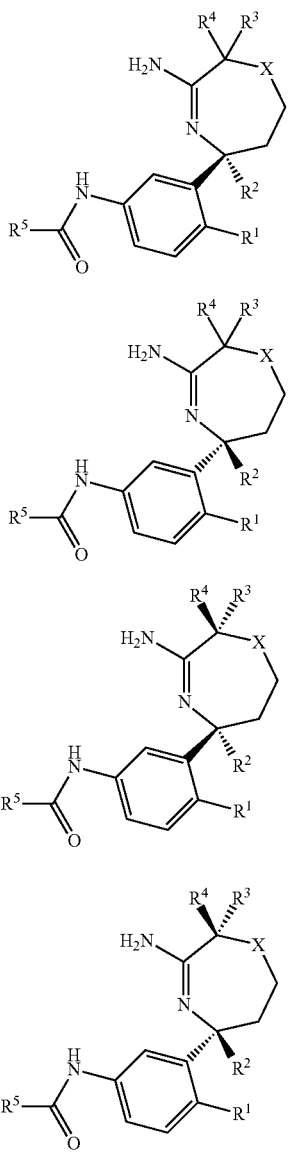

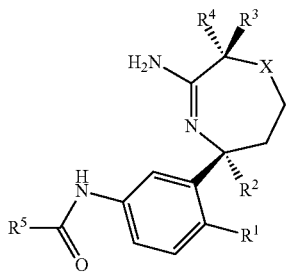

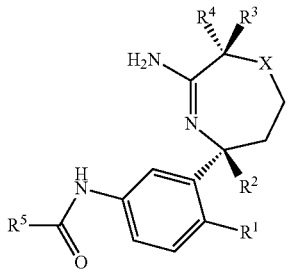

In the embodiments, where optically pure enantiomers are provided, optically pure enantiomer means that the compound contains >90% of the desired isomer by weight, preferably >95% of the desired isomer by weight, or more preferably >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following schemes. The starting material is commercially available or can be prepared in accordance with known methods. Any previously defined residues and variables will continue to have the previously defined meaning unless otherwise indicated.

The compounds of formula I can be prepared through a number of synthetic routes for example as illustrated in below schemes. The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes described below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Some typical procedures for the preparation of compounds of formula I are illustrated in Schemes A, B and C:

Sulfinyl imines of formula A2 can be prepared in analogy to T. P. Tang & J. A. Ellman, J. Org. Chem. 1999, 64, 12, by condensation of an aryl ketone and a sulfinamide, e.g. an alkyl sulfinamide, most preferably (R)-(+)-tert-butylsulfinamide in the presence of a Lewis acid such as e.g. a titanium(IV) alkoxyde, more preferably titanium(IV)ethoxide, in a solvent such as an ether, e.g. diethyl ether or more preferably THF.

The conversion of the sulfinyl imine A2 to the sulfinamide ester A3 proceeds stereoselectively by the chiral directing group as described by Tang & Ellman. The sulfinyl imine A2 can be reacted with a titanium enolate generated from e.g. an alkyl acetate, preferably ethyl acetate, LDA and chlorotriisopropoxytitanium at low temperature, preferably at −78° C. in a solvent such as an ether, e.g. diethyl ether or more preferably THF. Alternatively sulfinamide ester A3 can be produced from sulfinyl imine A2 by Reformatsky reaction of a bromoacetic ester derivative and zinc dust, optionally in the presence of copper(I) chloride, in a solvent such as an ether, e.g. diethyl ether or more preferably THF, at temperatures from 0 to 70° C., preferably at 23° C.

Sulfinamide ester A3 can be reduced to the alcohol A4 by the reduction of the ethylester with an alkali hydride, preferably lithium borohydride or lithium aluminium hydride in a solvent such as an ether, e.g. diethyl ether or more preferably THF.

The thioacetate A5 can be prepared from the alcohol A4 by a Mitsunobu protocol using thioacetic acid, triphenylphosphine and a diazocarboxylate, preferably DCAD or DEAD in a solvent such as dichloromethane.

The preparation of the sulfinamide nitrile A6 can be accomplished from the thioacetate A5 by cleavage of the thioacetate in the presence of the alkylating reagent, such as halide acetonitrile analogs, with a mineral base, preferably $K_2CO_3$ in a solvent such as methanol.

Hydrolysis of the chiral directing group in the sulfinamide nitrile A6 to give the amino nitrile A7 can be accomplished with a mineral acid, e.g. sulfuric acid or preferably hydrochloric acid in a solvent such as an ether, e.g. diethyl ether or more preferably 1,4-dioxane.

Aminothiazepine A8 can be prepared by the reaction of amino nitrile A7 and trimethyl aluminium in a solvent such as a xylene, preferably toluene.

The reduction of the nitro group in aminothiazepine A8 to the aniline A9 can be accomplished by metal reduction such as iron or tin, more preferably Tin chloride in alcohol, more preferably aqueous ethanol at elevated temperature, more preferably 80° C.

Amide coupling of the aniline A9 and a carboxylic acid to give the amide A10 can be effected with a carbodiimide, e.g. DCC or EDCI or a triazine, such as DMTMM in a solvent such as dichloromethane or methanol respectively.

The preparation of the sulfone A11 can be accomplished from the amide A10 by treatment with a peroxide, preferably meta-chloroperbenzoic acid, in a solvent such as dichloromethane.

Scheme A

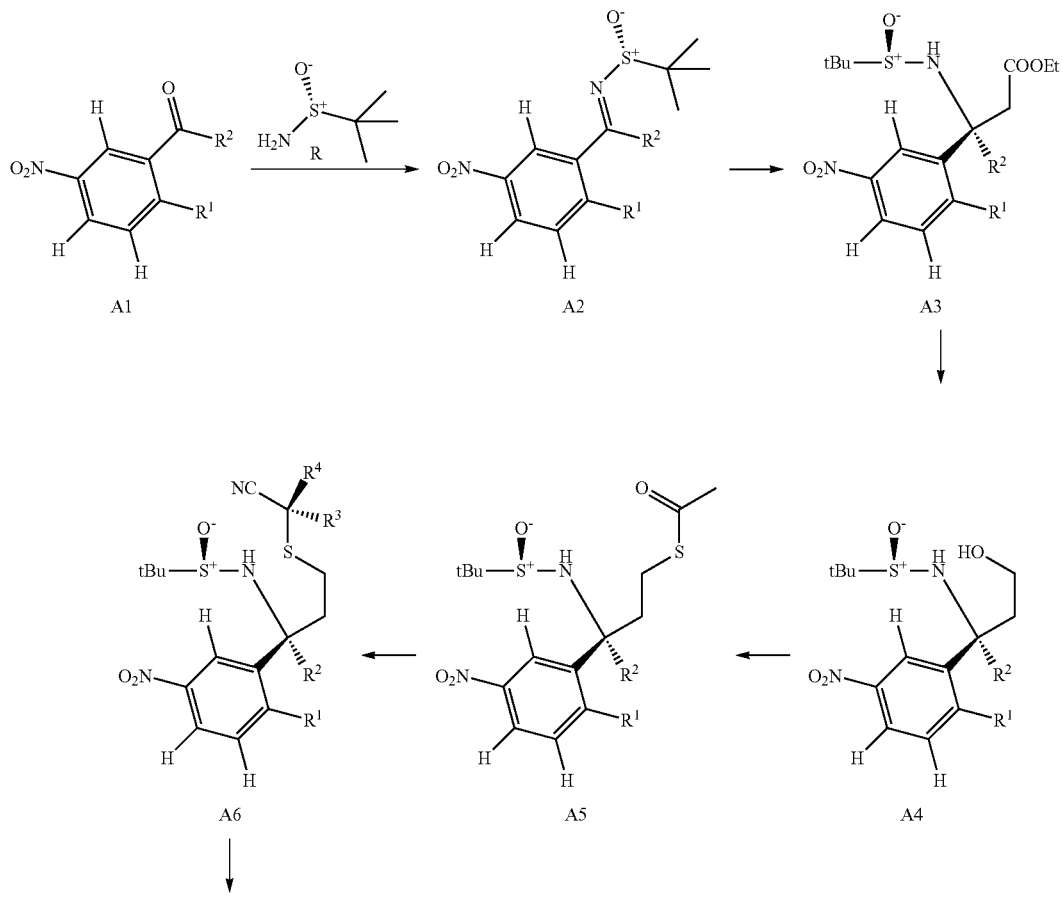

-continued
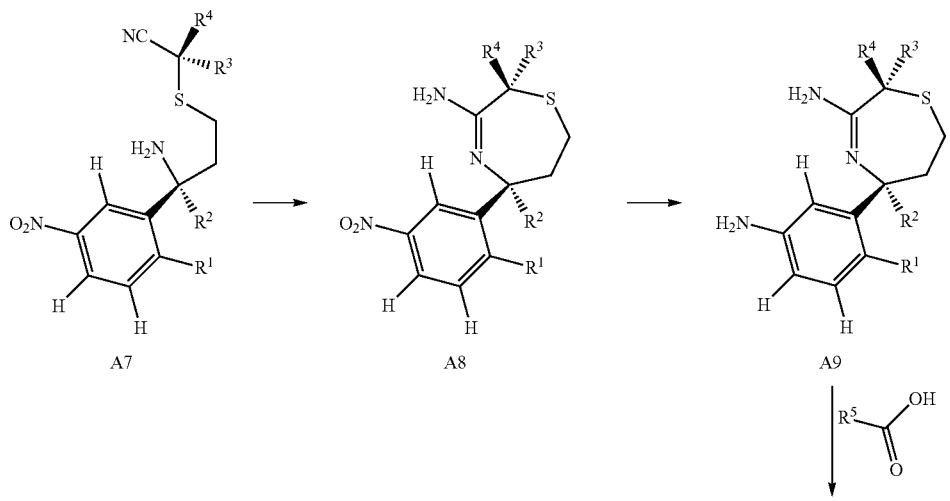
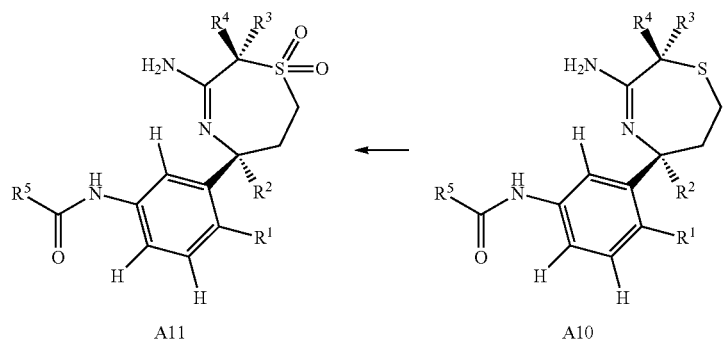
Scheme B
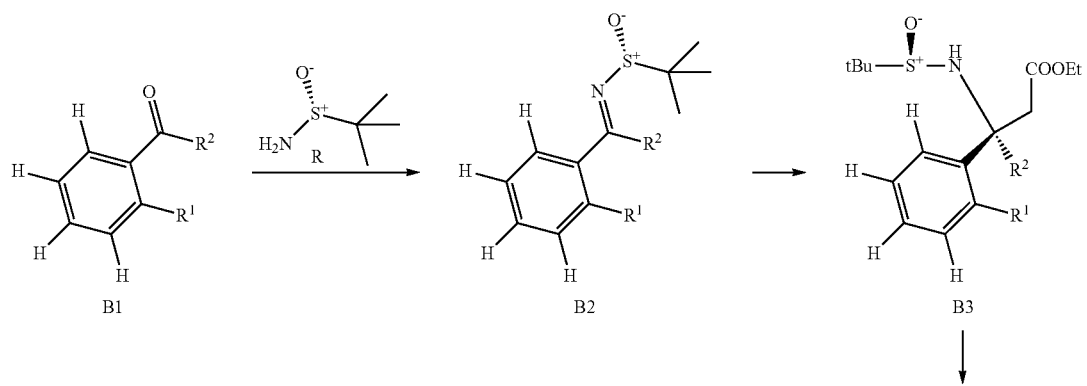

-continued

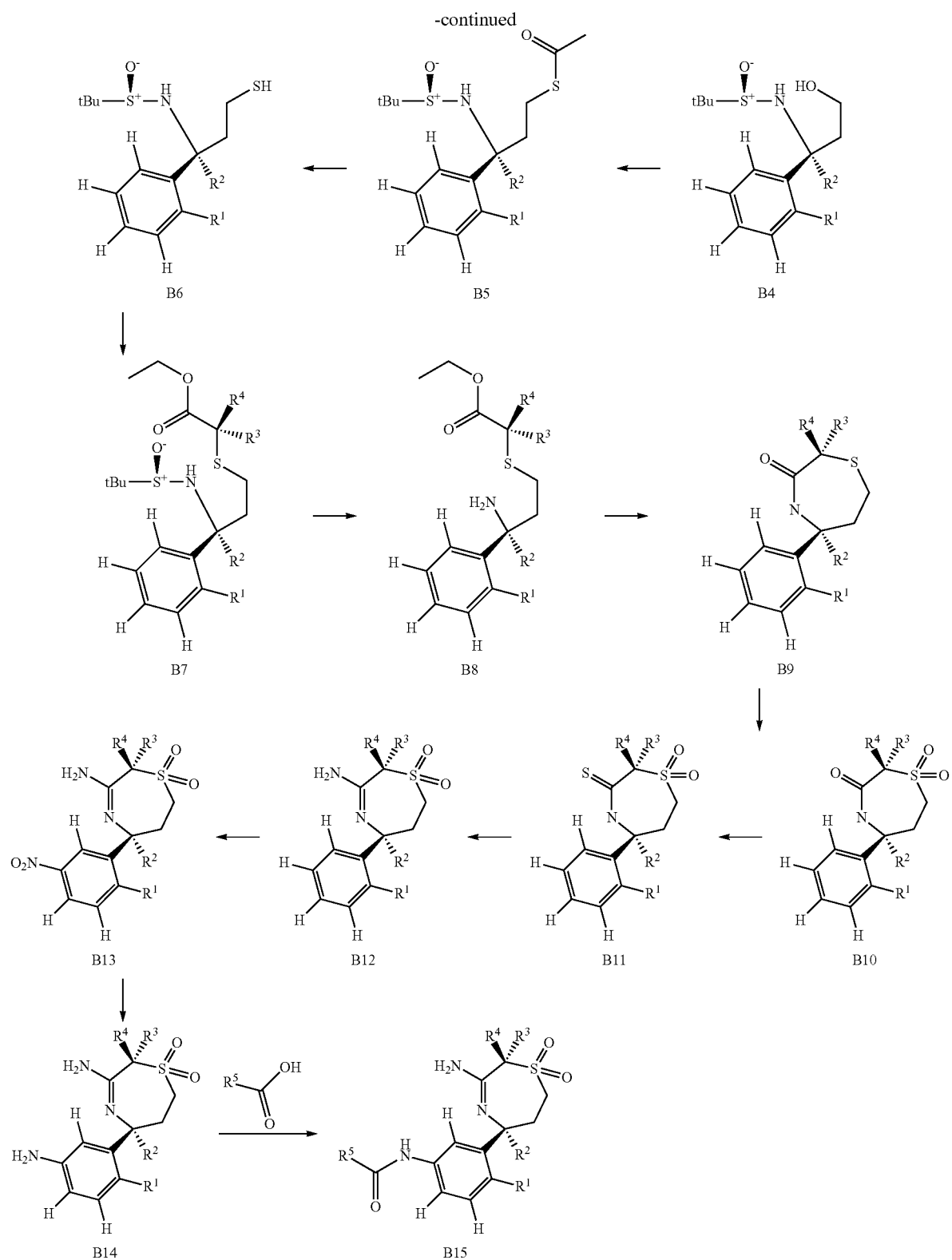

Sulfinyl imines of formula B2 can be prepared in analogy to T. P. Tang & J. A. Ellman, J. Org. Chem. 1999, 64, 12, by condensation of an aryl ketone and a sulfinamide, e.g. an alkyl sulfinamide, most preferably (R)-(+)-tert-butylsulfinamide in the presence of a Lewis acid such as e.g. a titanium(IV) alkoxyde, more preferably titanium(IV)ethoxide in a solvent such as an ether, e.g. diethyl ether or more preferably THF.

The conversion of the sulfinyl imine B2 to the sulfinamide ester B3 proceeds stereoselectively by the chiral directing group as described by Tang & Ellman. The sulfinyl imine B2 can be reacted with a titanium enolate generated from e.g. an alkyl acetate, preferably ethyl acetate, LDA and chlorotriisopropoxytitanium at low temperature, preferably at −78° C. in a solvent such as an ether, e.g. diethyl ether or more preferably THF. Alternatively sulfinamide ester B3 can be produced from sulfinyl imine B2 by Reformatsky reaction of a bromoacetic ester derivative and zinc dust, optionally in the presence of copper(I) chloride, in a solvent such as an ether, e.g. diethyl ether or more preferably THF, at temperatures from 0 to 70° C., preferably at 23° C.

Sulfinamide ester B3 can be reduced to the alcohol B4 by the reduction of the ethylester with an alkali hydride, preferably lithium borohydride or lithium aluminium hydride in a solvent such as an ether, e.g. diethyl ether or more preferably THF.

The thioacetate B5 can be prepared from the alcohol B4 by a Mitsunobu protocol using thioacetic acid, triphenylphosphine and a diazocarboxylate, preferably DCAD or DEAD in a solvent such as dichloromethane.

The thiol B6 can be prepared from the thioacetate B5 by cleavage of the acetate using a mineral base, such as potassium carbonate in methanol as a solvent.

The thiol B6 can be alkylated to the ester B7 using an alkylating reagent such as α-halide ester analogs with a mineral base, such as potassium carbonate in acetonitrile as the solvent.

Hydrolysis of the chiral directing group in the ester B7 to give the amino ester B8 can be accomplished with a mineral acid, e.g. sulfuric acid or preferably hydrochloric acid in a solvent such as ethanol, at temperatures from 0 to 23° C.

The amino ester B8 can be cyclized to the lactam B9 using a base such as bis[bis(trimethylsilyl)amino]tin(II) in a etheral solvent, preferably THF, at temperature from 23° C. to 50° C.

The thioether B9 can be oxidized to the sulfone B10 by treatment with an oxidizing reagent, preferably meta-chloroperbenzoic acid, in dichloromethane as a solvent at room temperature.

The thiolactam B11 can be prepared from the sulfone B10 using Lawesson's reagent in a etheral solvent such as dioxane or preferably THF at reflux.

The 1,1-dioxo-[1,4]thiazepine B12 can be prepared from the thiolactam B11 by treatment with mercury(II) chloride and a solution of ammonia in methanol in a solvent such as THF at a temperature of 120° C. in a micro-wave cavity.

Introduction of the nitro group in 1,1-dioxo-[1,4]thiazepine B12 to give B13 was best performed according to the standard procedure involving sulfuric acid and nitric acid at low temperature, preferably at 0° C.

The reduction of the nitro group in B13 to the aniline B14 can be accomplished by metal reduction such as iron or tin, more preferably tin chloride in alcohol, more preferably aqueous ethanol at elevated temperature, more preferably 80° C.

Amide coupling of the aniline B14 and a carboxylic acid to give the amide B15 (=A11) can be effected with a carbodiimide, e.g. DCC or EDCI or a triazine, such as DMTMM in a solvent such as dichloromethane or methanol respectively.

Scheme C

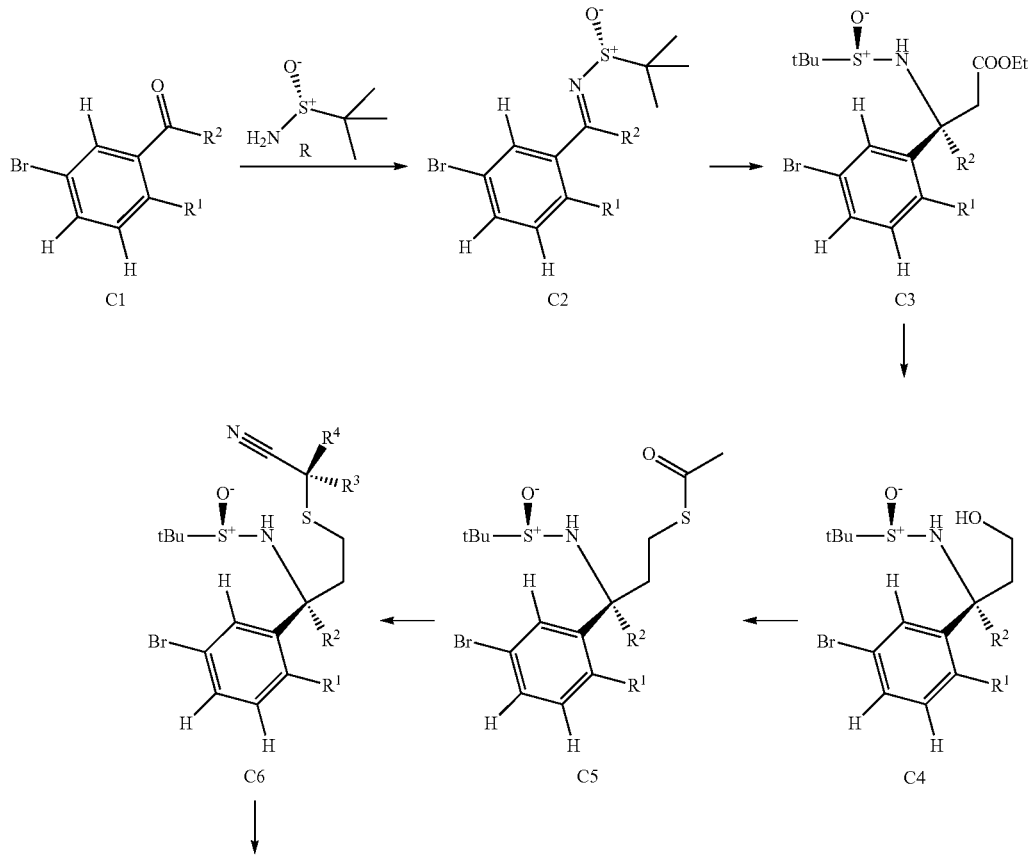

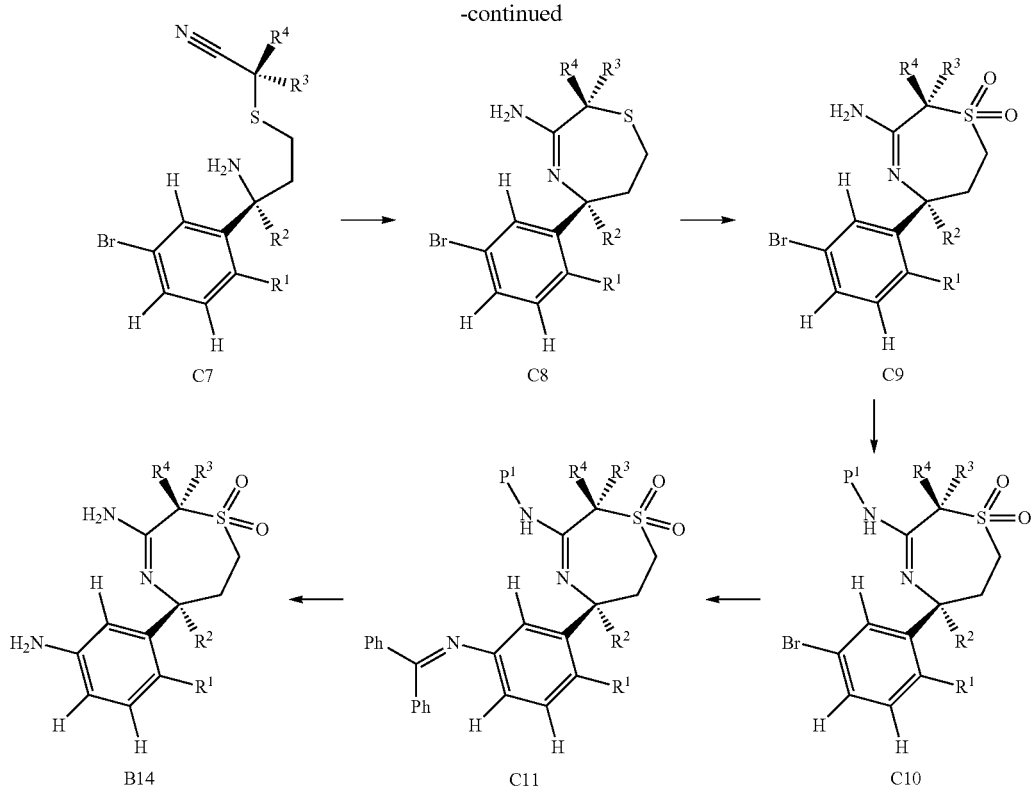

Sulfinyl imines of formula C2 can be prepared in analogy to T. P. Tang & J. A. Ellman, J. Org. Chem. 1999, 64, 12, by condensation of an aryl ketone and a sulfinamide, e.g. an alkyl sulfinamide, most preferably (R)-(+)-tert-butylsulfinamide in the presence of a Lewis acid such as e.g. a titanium(IV) alkoxide, more preferably titanium(IV)ethoxide in a solvent such as an ether, e.g. diethyl ether or more preferably THF.

The conversion of the sulfinyl imine C2 to the sulfinamide ester C3 proceeds stereoselectively by the chiral directing group as described by Tang & Ellman. The sulfinyl imine C2 can be reacted with a titanium enolate generated from e.g. an alkyl acetate, preferably ethyl acetate, LDA and chlorotriisopropoxytitanium at low temperature, preferably at −78° C. in a solvent such as an ether, e.g. diethyl ether or more preferably THF. Alternatively sulfinamide ester C3 can be produced from sulfinyl imine C2 by Reformatsky reaction of a bromoacetic ester derivative and zinc dust, optionally in the presence of copper(I) chloride, in a solvent such as an ether, e.g. diethyl ether or more preferably THF, at temperatures from 0 to 70° C., preferably at 23° C.

Sulfinamide ester C3 can be reduced to the alcohol C4 by the reduction of the ethylester with an alkali hydride, preferably lithium borohydride or lithium aluminum hydride in a solvent such as an ether, e.g. diethyl ether or more preferably THF.

The thioacetate C5 can be prepared from the alcohol C4 by a Mitsunobu protocol using thioacetic acid, triphenylphosphine and a diazocarboxylate, preferably DCAD or DEAD in a solvent such as dichloromethane.

The preparation of the sulfinamide nitrile C6 can be accomplished from the thioacetate C5 by cleavage of the thioacetate in the presence of the alkylating reagent, such as halide acetonitrile analogs, with a mineral base, preferably $K_2CO_3$ in a solvent such as methanol.

Hydrolysis of the chiral directing group in the nitrile C6 to give the amino nitrile C7 can be accomplished with a mineral acid, e.g. sulfuric acid or preferably hydrochloric acid in a solvent such as dioxane, THF, ethyl acetate or methanol, at temperatures from 0 to 23° C.

The amino nitrile C7 can be cyclized to the amidine C8 using a Lewis acid such as trimethylaluminum in an inert solvent, preferably toluene, at temperatures from 23° C. to 100° C., preferably 60° C.

The thioether C8 can be oxidized to the sulfone C9 by treatment with an oxidizing reagent, preferably meta-chloroperbenzoic acid, in dichloromethane as a solvent at room temperature. Alternatively the oxidation can be carried out using potassium peroxymonosulfate (Oxone) in a solvent such as methanol at ambient temperature.

Protection of the amino group in compounds of formula C9, to produce aryl bromides of formula C10 can be performed with triarylmethyl chlorides, such as triphenylmethyl chloride (Tr-Cl), p-methoxyphenyldiphenylmethyl chloride (MMTr-Cl), di(p-methoxyphenyl)phenylmethyl chloride (DMTr-Cl) or tri(p-methoxyphenyl)methyl chloride (TMTr-Cl), preferably DMTr-Cl, under basic conditions, e.g. in the presence of an amine, such as triethylamine or diisopropylethylamine, in a chlorinated solvent, such as dichloromethane or chloroform, at temperatures between 0° C. and ambient temperature.

Aryl bromides of formula C10 can be reacted with ammonia equivalents, such as benzophenone imine, in the presence of a suitable transition metal catalyst, such as bis(dibenzylideneacetone)palladium (0) ((dba)$_2$Pd) or tris(dibenzylideneacetone) dipalladium (0) ((dba)$_3$Pd$_2$)), and a suitable ligand, such as rac-2,2'-bis(diphenylphosphino)-1,1'-binaphthyl (rac-BINAP), 2-dicyclohexylphosphino-2',4',6'-triisopropylbiphenyl (X-PHOS) or 2-di-tert-butylphosphino-2',4', 6'-triisopropylbiphenyl (t-Bu X-PHOS), in the presence of a base, such as sodium tert-butoxide, potassium phosphate or cesium carbonate, in a suitable solvent, such as toluene or 1,4-dioxane, under an inert atmosphere, such as nitrogen or argon, at temperatures between 80 and 110° C., to produce compounds of formula C11.

Deprotection of both amino groups in compounds of formula C11 can be achieved by a one-pot procedure by first reacting it with a strong organic acid, such as trifluoroacetic acid, in chlorinated solvents, such as dichloromethane or chloroform, under anhydrous conditions at temperatures between 0° C. and ambient temperature to cleave the $P^1$-group. Then the addition of water or aqueous hydrochloric acid to cleave the benzophenone imine and reaction at ambient temperature produces diamines of formula B14.

Scheme D

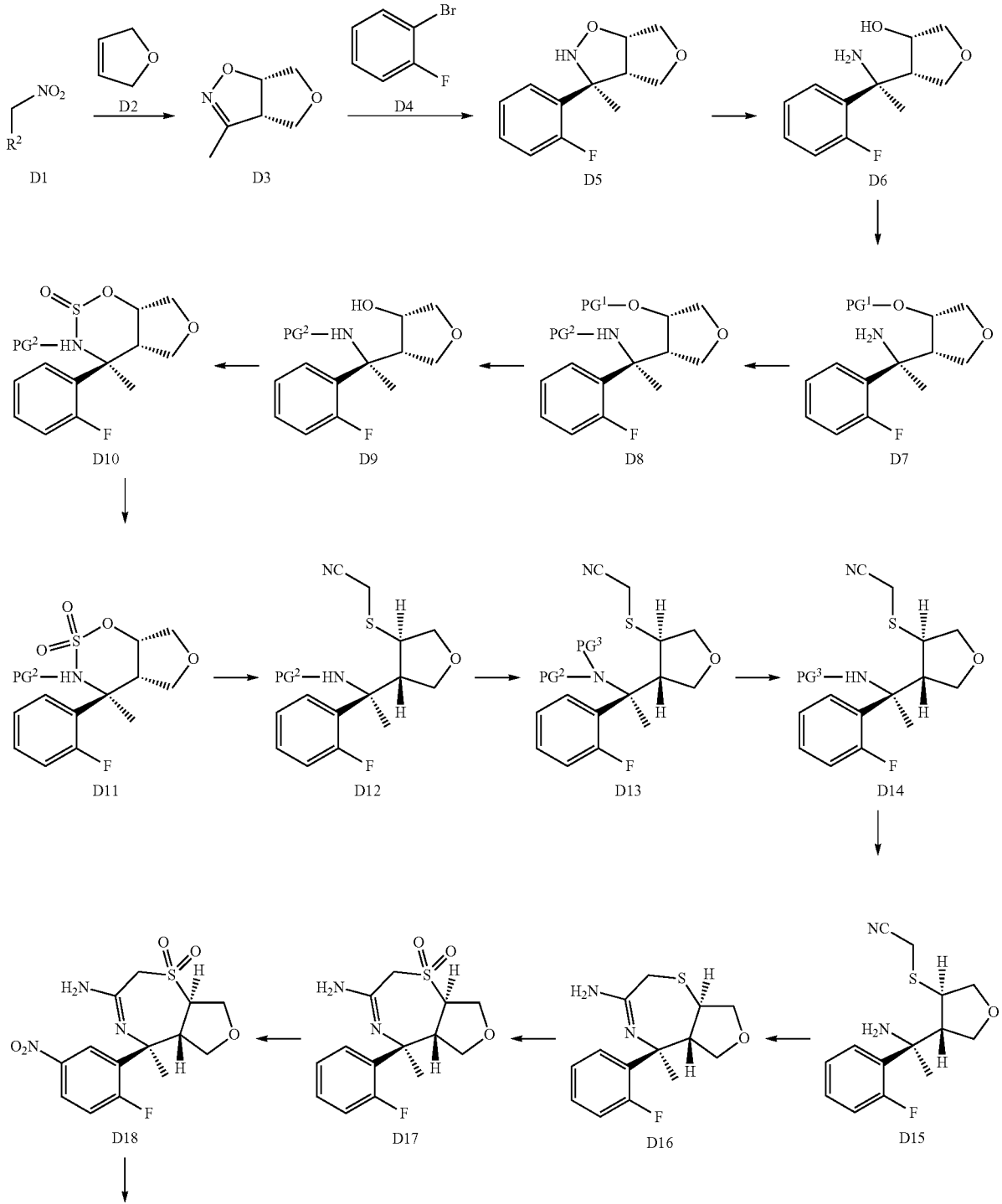

-continued

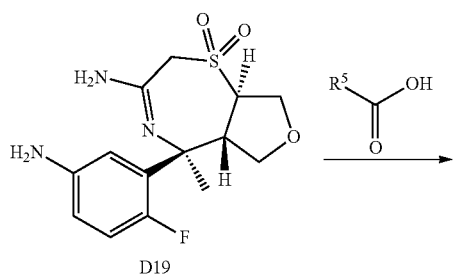 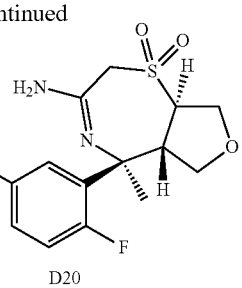

D19                                                    D20

Anellated compounds of formula D20 can be prepared as described in scheme D. The starting material is commercially available or can be prepared in accordance with known methods. Any previously defined residues and variables will continue to have the previously defined meaning unless otherwise indicated.

The nitro compound D1 is reacted with olefine D2 in the presence of an activating reagent such as e.g. an isocyanate, in particular phenylisocyanate, and a catalytic amount of a base, in particular an alkyl amine, more particularly Et$_3$N, in a solvent such as benzene or toluene, in particular benzene, or an alkyl ether, in particular diethyl ether, or a chlorinated solvent, in particular dichloromethane, to give the dihydroisoxazole D3.

Arylation of the dihydroisoxazole D3 with the arylbromide D4 to give the isoxazolidine D5 is performed by reacting an arylhalide, in particular an arylbromide, with an alkyl lithium reagent, in particular n-BuLi, to give an aryllithium species, which can be reacted with the dihydroisoxazole D3 in the presence of a Lewis base, preferably boron trifluoride etherate in a solvent mixture consisting of an ether, in particular THF, and toluene at −100° C. to −20° C., in particular at −78° C.

Resolution of the racemic isoxazolidine D5 to give the chiral isoxazolidine can be done by chiral high-performance liquid chromatography (HPLC) using a Chiralpack AD column in a mixture of n-heptane and ethanol as the eluent.

Hydrogenolysis of the isoxazolidine D5 to the aminoalcohol D6 can be accomplished best by transfer hydrogenolysis using a Pd-catalyst, in particular Pd on carbon, and a hydrogen source, e.g. a salt of formic acid, in particular ammonium formate in a protic solvent such as an alcohol, in particular ethanol.

Aminoalcohol D6 can be selectively protected on the oxygen by O-silylation to the O-silylated aminoalcohol D7 with a chlorosilane, in particular ten-butylchlorodimethylsilane (PG$^1$=t-BuMe$_2$Si), in a chlorinated solvent such as dichloromethane in the presence of an trialkylamine base, in particular triethylamine, and a pyridine catalyst, in particular 4-dimethylaminopyridine, at 0° C. to 23° C.

The O-silylated aminoalcohol D7 can be reductively aminated to the O-silylated N-benzylated aminoalcohol D8 with an aldehyde, in particular p-methoxybenzaldehyde (PG$^2$=PMB) or 2,4-dimethoxybenzaldehyde (PG$^2$=DMB), using a reducing agent, in particular sodium cyanoborohydride or sodium triacetoxyborohydride, in a chlorinated solvent, in particular 1,2-dichloroethane or dichloromethane, in the presence of a weak organic acid, in particular acetic acid, at 0° C. to 60° C., preferably 23° C.

The O-silylated N-benzylated aminoalcohol D8 can be desilylated to the N-benzylated aminoalcohol D9 by reacting it with a fluoride source, in particular tetrabutylammonium fluoride (TBAF), in a solvent such as THF at 0° C. to 50° C., preferably at 23° C.

The N-benzylated aminoalcohol D9 can be reacted with thionyl chloride to the cyclic sulfamidite D10 in the presence of an amine base, in particular pyridine, in a chlorinated solvent, in particular dichloromethane, starting at low temperature such as −78° C. and warming up to 0° C. or ambient temperature.

The cyclic sulfamidite D10 can be oxidized to the cyclic sulfamidate D11 by an alkali periodate, such as sodium or potassium periodate, in the presence of a ruthenium salt, such as ruthenium(III) chloride, in solvent mixtures consisting of water, acetonitrile and ethyl acetate or tetrachloromethane at temperatures between 0° C. and 50° C., preferably at 23° C.

The cyclic sulfamidate D11 can be regio- and stereoselectively opened with a sulfur nucleophile, such as mercaptoacetonitrile, and subsequently hydrolyzed under acidic conditions to the N-benzylated amino nitrile D12. The ring opening proceeds in the presence of an amine base, such as 1,8-diazabicyclo[5.4.0]undec-7-ene (DBU) or 1,1,3,3-tetramethylguanidine (TMG), in a polar aprotic solvent, such as N,N-dimethylformamide, at temperatures between 23° C. and 80° C., preferably at 60° C. After removal of all volatiles from the ring opening step under vacuum by evaporation the crude reaction mixture is subjected to acidic hydrolysis in a mixture of a mineral acid, in particular 20% aqueous sulfuric acid, and a solvent such as diethyl ether or dichloromethane at temperatures between 0° C. and 50° C., preferably at 23° C.

The N-benzylated amino nitrile D12 is deprotected to the amino nitrile D15 in a three-step protocol: First, the N-benzylated amino nitrile D12 is reacted with an organic anhydride, in particular trifluoroacetic anhydride, in the presence of an amine base, in particular triethylamine or diisopropylethylamine, in a chlorinated solvent such as dichloromethane at temperatures between 0° C. and 40° C., preferably at 23° C. to give the N-benzylated N-trifluoroacetylated amino nitrile D13. Second, the N-benzylated N-trifluoroacetylated amino nitrile D13 is debenzylated to the N-trifluoroacetylated amino nitrile D14 by neat reaction with a strong organic acid, in particular trifluoroacetic acid, at temperatures between 0° C. and 50° C., preferably at 23° C. Third, the N-trifluoroacetylated amino nitrile D14 is deacylated to the amino nitrile D15 by treatment with a reducing agent, such as sodium borohydride, in an alcoholic solvent, in particular methanol or ethanol, at temperatures between 0° C. and 60° C., preferably at 23° C.

The amino nitrile D15 can be cyclized to the amidine D16 using a Lewis acid such as trimethylaluminum in an inert solvent, preferably toluene, at temperatures from 23° C. to 100° C., preferably 60° C.

The thioether D16 can be oxidized to the sulfone D17 by treatment with an oxidizing reagent, preferably meta-chloroperbenzoic acid, in dichloromethane as a solvent at room temperature. Alternatively the oxidation can be carried out using potassium peroxymonosulfate (Oxone) in a solvent such as methanol at ambient temperature.

The nitration of the amidine D17 to give the nitro-amidine D18 follows a standard procedure involving neat sulfuric acid and fuming nitric acid without using a solvent at temperatures between 0° C. and 23° C.

The reduction of the nitro group in the intermediate D18 to give the aniline D19 can be accomplished by hydrogenation using a catalyst such as Pd on carbon in protic solvents, such as alcohols, in particular ethanol or methanol.

Selective amide coupling of the aniline D19 and a carboxylic acid to give the amide D20 can be effected with 4-(4,6-dimethoxy[1.3.5]triazin-2-yl)-4-methylmorpholinium chloride (DMTMM) hydrate in a solvent such as an alcohol, in particular methanol.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of formula I in this invention can be derivatized at functional groups to provide derivatives which are capable of conversion back to the parent compound in vivo.

Pharmacological Tests

The compounds of formula I and their pharmaceutically acceptable salts possess valuable pharmacological properties. The compounds of the present invention are associated with inhibition of BACE1 and/or BACE2 activity. The compounds were investigated in accordance with the test given hereinafter.

Cellular Aβ-Lowering Assay:

Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96 well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/ $H_2O_2$ in citric acid buffer. After stopping the reaction with one volume 1 N $H_2SO_4$ the reaction was measured in an ELISA reader at 450 nm wavelength. The concentrations of Aβ in the culture supernatants were calculated from a standard curve obtained with known amounts of pure Aβ peptide.

Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+Glutamax (Invitrogen) Penicillin/Streptomycin, 10% Fetal bovine serum, 100 mM pyruvate, 5 mM beta-mercatptoethanol, 100 micrograms/ml G418 and 100 microgram/ml hygromycin and are grown inadherent culture at 37° C. in a standard $CO_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

TABLE 1

$IC_{50}$ values of selected examples

| Exam. | Structure | BACE2 $IC_{50}$ [μM] | BACE1 $IC_{50}$ [μM] |
|---|---|---|---|
| 1 | 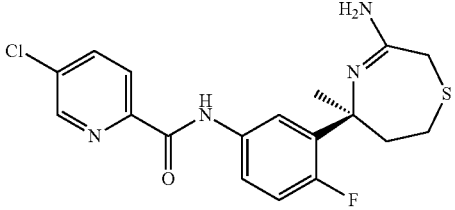 [SMILES: C[C@@]1(c2cc(NC(=O)c3ccc(Cl)cn3)ccc2F)CCSCC(N)=N1] | 0.167 | 0.0063 |

TABLE 1-continued

IC$_{50}$ values of selected examples

| Exam. | Structure | BACE2 IC$_{50}$ [µM] | BACE1 IC$_{50}$ [µM] |
|---|---|---|---|
| 2 | 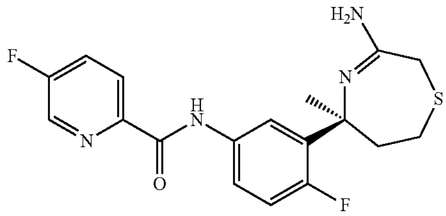 [SMILES: C[C@@]1(c2cc(NC(=O)c3ccc(F)cn3)ccc2F)CCSCC(N)=N1] | 0.079 | 0.016 |
| 3 | 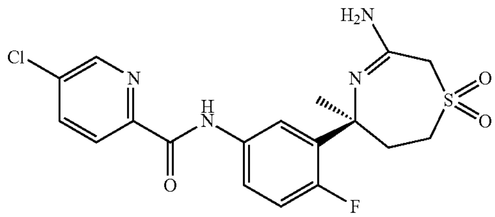 [SMILES: C[C@@]1(c2cc(NC(=O)c3ccc(Cl)cn3)ccc2F)CCS(=O)(=O)CC(N)=N1] | 0.005 | 0.003 |
| 4 | 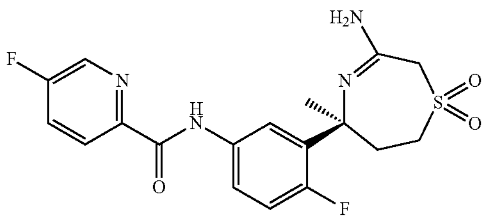 [SMILES: C[C@@]1(c2cc(NC(=O)c3ccc(F)cn3)ccc2F)CCS(=O)(=O)CC(N)=N1] | 0.004 | 0.02 |
| 5 | 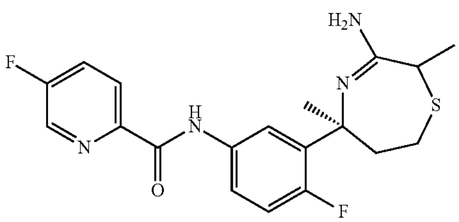 [SMILES: CC1SCC[C@@](C)(c2cc(NC(=O)c3ccc(F)cn3)ccc2F)N=C1N] | 0.021 | 0.17 |
| 6 | 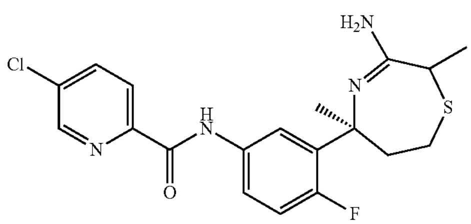 [SMILES: CC1SCC[C@@](C)(c2cc(NC(=O)c3ccc(Cl)cn3)ccc2F)N=C1N] | 0.009 | 0.14 |
| 7 | 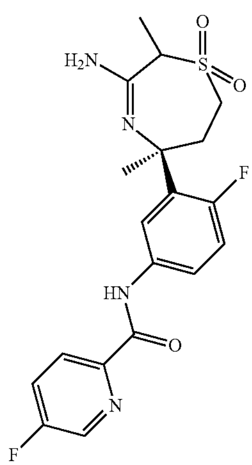 [SMILES: CC1C(N)=N[C@](C)(c2cc(NC(=O)c3ccc(F)cn3)ccc2F)CCS1(=O)=O] | 0.002 | 0.004 |

TABLE 1-continued

IC$_{50}$ values of selected examples

| Exam. | Structure | BACE2 IC$_{50}$ [μM] | BACE1 IC$_{50}$ [μM] |
|---|---|---|---|
| 8 | 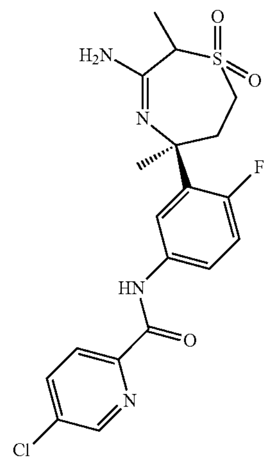 [SMILES: CC1C(N)=N[C@](C)(c2cc(NC(=O)c3ccc(Cl)cn3)ccc2F)CCS1(=O)=O] | 0.016 | 0.03 |
| 9 | 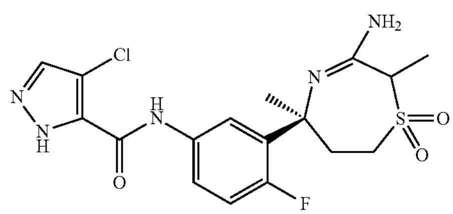 [SMILES: CC1C(N)=N[C@](C)(c2cc(NC(=O)c3[nH]ncc3Cl)ccc2F)CCS1(=O)=O] | 0.858 | 0.3 |
| 10 | 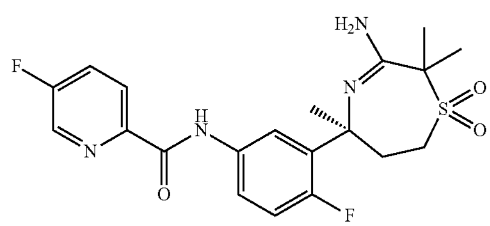 [SMILES: CC1(C)C(N)=N[C@](C)(c2cc(NC(=O)c3ccc(F)cn3)ccc2F)CCS1(=O)=O] | 0.181 | 0.062 |
| 11 | 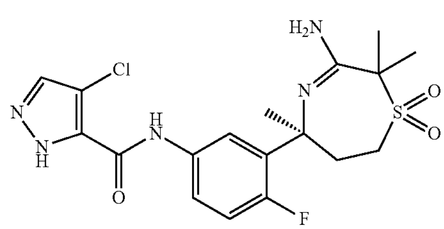 [SMILES: CC1(C)C(N)=N[C@](C)(c2cc(NC(=O)c3[nH]ncc3Cl)ccc2F)CCS1(=O)=O] | — | 2.290 |
| 12 | 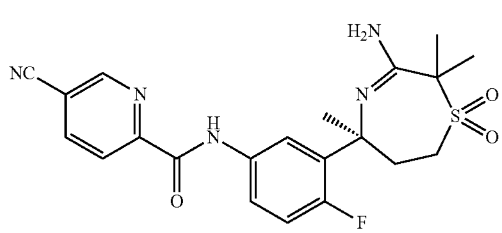 [SMILES: CC1(C)C(N)=N[C@](C)(c2cc(NC(=O)c3ccc(C#N)cn3)ccc2F)CCS1(=O)=O] | — | 0.053 |

TABLE 1-continued

IC$_{50}$ values of selected examples

| Exam. | Structure | BACE2 IC$_{50}$ [μM] | BACE1 IC$_{50}$ [μM] |
|---|---|---|---|
| 13 | (structure) | — | 0.260 |
| 14 | (structure) rac | — | 0.078 |

Pharmaceutical Compositions

The compounds of formula I and the pharmaceutically acceptable salts can be used as therapeutically active substances, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical compositions. Lactose, corn starch or derivatives thereof, talc, stearic acids or its salts and the like, can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, preferably 1-100 mg, of a compound of formula I. Examples of compositions according to the invention are:

EXAMPLE A

Tablets of the Following Composition are Manufactured in the Usual Manner

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the Following Composition are Manufactured

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

EXAMPLE B-2

Soft Gelatin Capsules of the Following Composition are Manufactured

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |

TABLE 5-continued possible soft gelatin capsule composition

| ingredient | mg/capsule |
|---|---|
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the Following Composition are Manufactured

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

EXAMPLE D

Injection Solutions of the Following Composition are Manufactured

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the Following Composition are Manufactured

TABLE 8

| possible sachet composition | |
| --- | --- |
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

General:

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

Abbreviations:

DCAD=Di-p-chlorobenzylazodicarboxylate; DCC=N,N'-dicyclohexyl-carbodiimide, DCE=1,2-dichloroethane, DCM=dichloromethane, DIPEA=diisopropylethylamine, DMAc=dimethylacetamide, DMAP=4-dimethylaminopyridine, DMF=N,N-dimethylformamide, DMSO=dimethyl sulfoxide, EDCI=N-(3-dimethylaminopropyl)-N'-ethyl-carbodiimide hydrochloride, HATU=1-[bis(dimethylamino)methylene]-1H-1,2,3-triazolo[4,5-b]pyridinium-3-oxide hexafluorophosphate, DMTMM=4-(4,6-Dimethoxy-1,3,5-triazin-2-yl)-4-methylmorpholinium chloride; HCl=hydrogen chloride, HPLC=high performance liquid chromatography, LDA=lithium diisopropylamide, MS=mass spectrum, NMR=nuclear magnetic resonance, TEA=triethylamine, TBME=tert-butyl methyl ether, and THF=tetrahydrofuran.

The following examples are provided for illustration of the invention. They should not be considered as limiting the scope of the invention, but merely as being representative thereof.

Synthesis of the intermediate sulfinyl imines A2

General Procedure

To a solution of the (R)-(+)-tert-butylsulfinamide (66 mmol) in THF (350 ml) was added subsequently the ketone A1 (72.6 mmol) and titanium(IV)ethoxide (132 mmol) and the solution was stirred at reflux temperature for 5 h. The mixture was cooled to 22° C., treated with brine (400 ml), the suspension was stirred for 10 min and filtered over dicalite. The layers were separated, the aqueous layer was extracted with ethyl acetate, the combined organic layers were washed with water, dried and concentrated in vacuum. The residue was purified by chromatography on silica using cyclohexane/ethyl acetate to give the pure sulfinyl imine A2.

Intermediate A2A

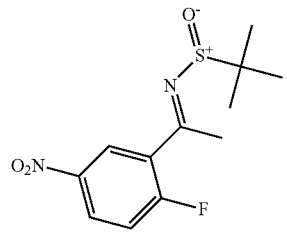

Starting from 1-(2-fluoro-5-nitro-phenyl)-ethanone, the product (R)-2-methyl-propane-2-sulfinic acid [1-(2-fluoro-5-nitro-phenyl)-eth-(E)-ylidene]-amide was obtained as a pale brown oil. MS (ISP): m/z=287.1 [M+H]$^+$.

Synthesis of the intermediate sulfinamide esters A3

General Procedure (Via Reformatsky Reaction)

In a dry apparatus a suspension of freshly activated zinc powder (1.63 g, 24.9 mmol) in dry THF (70 ml) was heated under inert atmosphere to reflux. A solution of the sulfinyl imine A2 (24.9 mmol) and the bromo-acetate (24.9 mmol) in dry THF (15 ml) was added dropwise over a period of 15 min and the suspension was heated to reflux for 5 h. The cooled mixture was partitioned between aqueous saturated NH$_4$Cl and ethyl acetate, the organic layer was dried and evaporated. The crude material was purified by flash chromatography using heptane/ethyl acetate to give the sulfinamide ester A3.

Intermediates A3A

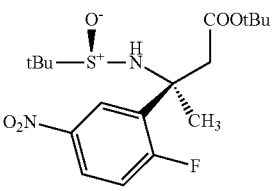

Starting from (R)-2-methyl-propane-2-sulfinic acid [1-(2-fluoro-5-nitro-phenyl)-eth-(E)-ylidene]-amide, the product (S)-3-(2-fluoro-5-nitro-phenyl)-(R)-3-(2-methyl-propane-2-sulfinylamino)-butyric acid tert-butyl ester was obtained as pale brown oil. MS (ISP): m/z=403.2 [M+H]$^+$.

Synthesis of the intermediate sulfinamide alcohols A4

General Procedure

A solution of the sulfinamide ester A3 (12.7 mmol) in dry THF (50 ml) was treated at 0° C. with lithium borohydride (25.3 mmol) and stirring was continued at 0° C. for 4 h. The reaction mixture was quenched by addition of acetic acid (2 ml) and water (50 ml), extracted with ethyl acetate and the organic layer was dried and evaporated. The residue was purified by chromatography on silica using a mixture of n-heptane and ethyl acetate to give the pure intermediate sulfinamide alcohol A4.

Intermediate A4A

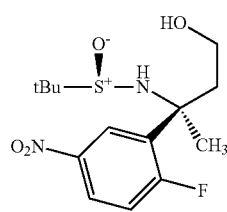 [SMILES: CC(C)(C)[S@+]([O-])N[C@@](C)(CCO)c1cc([N+](=O)[O-])ccc1F]

Starting from (S)-3-(2-fluoro-5-nitro-phenyl)-(R)-3-(2-methyl-propane-2-sulfinylamino)-butyric acid tert-butyl ester, the product (R)-2-methyl-propane-2-sulfinic acid [(S)-1-(2-fluoro-5-nitro-phenyl)-3-hydroxy-1-methyl-propyl]-amide was obtained as a yellow oil. MS (ISP): m/z=333.3 [M+H]⁺.

Synthesis of the intermediate sulfinamide thioacetate A5

General Procedure

A solution of triphenylphosphine (4.73 g, 18.1 mmol) in 50 ml dry DCM at 0° C. under argon was treated with DCAD (6.63 g, 18.1 mmol) and the resulting reaction mixture stirred at 0° C. for 20 min. To the previous reaction mixture was added a solution of thioacetic acid (1.37 mg, 18.1 mmol) and the alcohol A4 (3.0 g, 9.03 mmol) in 10 mL dry DCM. The reaction mixture was stirred for 20 min at 0° C., was let to warm up to room temperature and stirred for 18 h at that temperature. The white precipitate, which formed during the course of the reaction, was filtered off. The filtrate was diluted with more dichloromethane and extracted with a 1 M sodium carbonate aqueous solution. The organic layer was dried over sodium sulfate and evaporated down to dryness. The residue was purified by silica gel chromatography using a mixture of n-heptane and ethyl acetate to yield 3.2 g of pure product.

Intermediate A5A

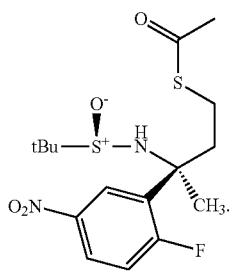 [SMILES: CC(=O)SCC[C@](C)(N[S@@+]([O-])C(C)(C)C)c1cc([N+](=O)[O-])ccc1F]

Starting from (R)-2-methyl-propane-2-sulfinic acid [(S)-1-(2-fluoro-5-nitro-phenyl)-3-hydroxy-1-methyl-propyl]-amide, the product thioacetic acid S—[(S)-3-(2-fluoro-5-nitro-phenyl)-(R)-3-(2-methyl-propane-2-sulfinylamino)-butyl]ester was obtained as a yellow oil. MS (ISP): m/z=391.3 [M+H]⁺.

Synthesis of the intermediate sulfinamide nitrile A6

General Procedure

A solution of thioacetate A5 (1.3 g, 3.33 mmol) in 19 ml methanol under argon was treated with bromo acetonitrile (2.23 g, 16.6 mmol) and potassium carbonate (460 mg, 3.33 mmol). The resulting reaction mixture was stirred at room temperature for one hour. The reaction medium was poured in to a separatory funnel filled with ethyl acetate and extracted with water, the organic layer was dried over sodium sulfate and evaporated down to dryness. The crude was purified by silica gel chromatography using a mixture of n-heptane and ethyl acetate to give 1.05 g of the sulfonamide nitrile A6.

Intermediate A6A

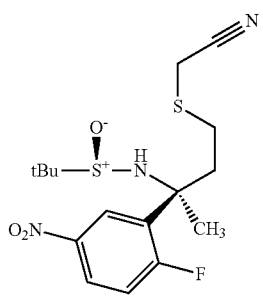 [SMILES: CC(C)(C)[S@+]([O-])N[C@@](C)(CCSCC#N)c1cc([N+](=O)[O-])ccc1F]

Starting from thioacetic acid S—[(S)-3-(2-fluoro-5-nitro-phenyl)-(R)-3-(2-methyl-propane-2-sulfinylamino)-butyl] ester, the product (R)-2-methyl-propane-2-sulfinic acid [(S)-3-cyanomethylsulfanyl-1-(2-fluoro-5-nitro-phenyl)-1-methyl-propyl]-amide was obtained as a yellow oil. MS (ISP): m/z=388.1 [M+H]⁺.

Intermediate A6B

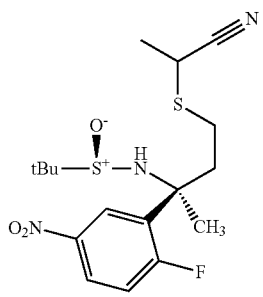 [SMILES: CC(C#N)SCC[C@](C)(N[S@@+]([O-])C(C)(C)C)c1cc([N+](=O)[O-])ccc1F]

Starting from thioacetic acid S—[(S)-3-(2-fluoro-5-nitro-phenyl)-(R)-3-(2-methyl-propane-2-sulfinylamino)-butyl] ester, the product (R)-2-methyl-propane-2-sulfinic acid [(S)-3-(cyano-methyl-methylsulfanyl)-1-(2-fluoro-5-nitro-phenyl)-1-methyl-propyl]-amide as a mixture of epimers was obtained as yellow oil. MS (ISP): m/z=402.1 [M+H]⁺.

Synthesis of the intermediate amino nitrile A7

General Procedure

A solution of sulfonamide nitrile (1 g, 2.49 mmol) in 20 ml MeOH at 0° C. was treated with a solution 4 M hydrochloric acid in dioxane (1.56 ml, 6.23 mmol) and reaction was stirred at 0° C. for 30 min until complete conversion to the desired product. The reaction mixture was diluted with ethyl acetate and extracted with a 2 M sodium carbonate aqueous solution. The organic layer was dried over sodium sulfate and evaporated down in vacuum to dryness. The crude was purified by silica gel chromatography using a mixture of n-heptane and ethyl acetate to give 502 mg of the amino nitrile A7.

Intermediate A7A

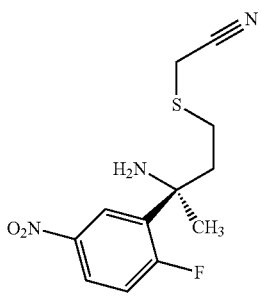 [SMILES: C[C@](N)(CCSCC#N)c1cc([N+](=O)[O-])ccc1F]

Starting from (R)-2-methyl-propane-2-sulfinic acid [(S)-3-cyanomethylsulfanyl-1-(2-fluoro-5-nitro-phenyl)-1-methyl-propyl]-amide, the product [(S)-3-amino-3-(2-fluoro-5-nitro-phenyl)-butylsulfanyl]-acetonitrile was obtained as a yellow oil. MS (ISP): m/z=284.3 [M+H]$^+$.

Intermediate A7B

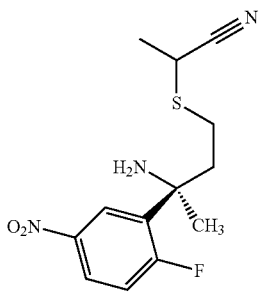 [SMILES: CC(C#N)SCC[C@](C)(N)c1cc([N+](=O)[O-])ccc1F]

Starting from (R)-2-methyl-propane-2-sulfinic acid [(S)-3-(cyano-methyl-methylsulfanyl)-1-(2-fluoro-5-nitro-phenyl)-1-methyl-propyl]-amide, the product 2-[(S)-3-amino-3-(2-fluoro-5-nitro-phenyl)-butylsulfanyl]-propionitrile was obtained as yellow oil. MS (ISP): m/z=298.0 [M+H]$^+$.

Synthesis of the intermediate 1,4-thiazepine A8

General Procedure

To a solution of amino nitrile A6 (0.715 g, 2.51 mmol) in 25 ml dry toluene at 0° C. was slowly added trimethylaluminum 2.0 M solution in toluene (1.26 ml, 2.51 mmol). The resulting reaction mixture was stirred for 30 min at 0° C. and finally stirred at 60° C. for a period of two hours. Reaction mixture was carefully quenched by addition of water at 0° C. and stirred for a period of 15 min, the precipitate formed was filtered over Celite. The filtrate was diluted with ethyl acetate, extracted with a 2 M sodium carbonate aqueous solution and the organic layer was dried over sodium sulfate and evaporated down to dryness. The crude was purified by silica gel chromatography using a mixture of n-heptane and ethyl acetate to give 575 mg of a yellow oil. Yield: 81%

Intermediate A8A

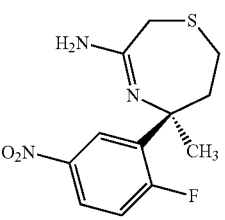 [SMILES: C[C@@]1(c2cc([N+](=O)[O-])ccc2F)CCSCC(N)=N1]

Starting from [(S)-3-amino-3-(2-fluoro-5-nitro-phenyl)-butylsulfanyl]-acetonitrile, the product (S)-5-(2-fluoro-5-nitro-phenyl)-5-methyl-2,5,6,7-tetrahydro-[1,4]thiazepin-3-ylamine was obtained as a yellow oil. MS (ISP): m/z=284.3 [M+H]$^+$.

Intermediate A8B

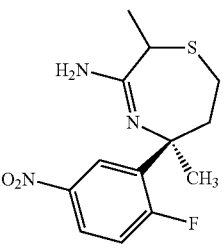

Starting from 2-[(S)-3-amino-3-(2-fluoro-5-nitro-phenyl)-butylsulfanyl]-propionitrile, the product (S)-5-(2-fluoro-5-nitro-phenyl)-2,5-dimethyl-2,5,6,7-tetrahydro-[1,4]thiazepin-3-ylamine was obtained as a yellow oil. MS (ISP): m/z=298.3 [M+H]$^+$.

Synthesis of the intermediate aniline A9

General Procedure

To a solution of nitrobenzene A7 (140 mg, 0.47 mmol) in 4.0 ml EtOH was added SnCl$_2$.2H$_2$O (321 mg, 1.42 mmol) (precipitate formed instantly which dissolved upon heating). Reaction stirred at 80° C. for 1.5 h and controlled by TLC Si—NH$_2$ (CH$_2$Cl$_2$/MeOH/NH$_4$OH 80:18:2) which showed complete conversion. Reaction mixture poured into an aqueous solution NaOH 1N, addition of ethyl acetate and the mixture was stirred for 10 min. Precipitate was filtered over Celite, the two phases in the filtrate were separated. The organic phase was dried over Na$_2$SO$_4$, filtered and evaporated down to dryness. The residue was purified by chromatography on an amine-modified silica with a mixture of $CH_2Cl_2$ and MeOH to give the pure aniline.

Intermediate A9A

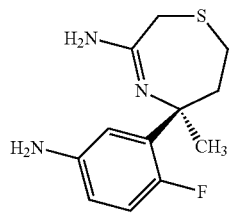

Starting from (S)-5-(2-fluoro-5-nitro-phenyl)-5-methyl-2,5,6,7-tetrahydro-[1,4]thiazepin-3-ylamine, the product (S)-5-(5-amino-2-fluoro-phenyl)-5-methyl-2,5,6,7-tetrahydro-[1,4]thiazepin-3-ylamine was obtained as colorless oil. MS (ISP): m/z=254.3 $[M+H]^+$.

Intermediate A9B

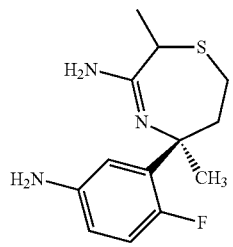 [SMILES: CC1SCC[C@@](C)(c2cc([N+](=O)[O-])ccc2F)N=C1N]

Starting from (S)-5-(2-fluoro-5-nitro-phenyl)-2,5-dimethyl-2,5,6,7-tetrahydro-[1,4]thiazepin-3-ylamine, the product (S)-5-(5-amino-2-fluoro-phenyl)-2,5-dimethyl-2,5,6,7-tetrahydro-[1,4]thiazepin-3-ylamine was obtained as a colorless oil. MS (ISP): m/z=268.1 $[M+H]^+$.

Synthesis of the intermediate amide A10

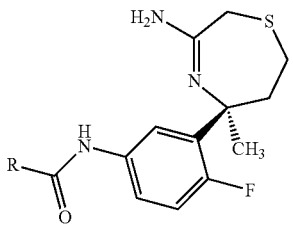

General Procedure

To a solution of the acid (0.16 mmol) in MeOH (1 ml) was added at 22° C. 4-(4,6-dimethoxy-1,3,5-triazin-2-yl)-4-methyl-morpholiniumchloride (0.19 mmol) and stirring was continued at 0° C. for 30 min. To the mixture was added a solution of the aniline A9 (0.15 mmol) in MeOH (2 ml) and stirring was continued at 0° C. for 2 h. The mixture was diluted with saturated aqueous $Na_2CO_3$, the MeOH was evaporated and the aqueous solution was extracted with ethyl acetate. The organic layer was dried, evaporated and the residue was purified by on silica gel chromatography using a mixture of dichloromethane and a solution of 3% triethylamine in methanol.

Synthesis of the intermediate amide A11

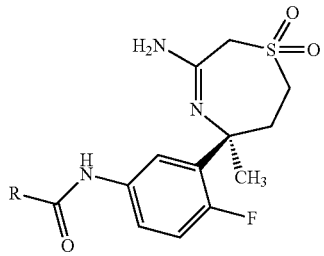

General Procedure

A solution of amide A10 (0.05 g, 0.133 mmol) in 1.5 ml dry $CH_2Cl_2$ at 0° C. was treated with m-CPBA (0.065 g, 0.266 mmol) and the resulting reaction mixture was stirred for a period of 1 h at room temperature. The reaction mixture was diluted with dichloromethane and extracted with a 2 M sodium carbonate aqueous solution. The organic layer was dried over sodium sulfate and evaporated down to dryness. The crude was purified by silica gel chromatography using a mixture of dichloromethane and a solution of 3% triethylamine in methanol.

Synthesis of the intermediate sulfinyl imines B2

General Procedure

To a solution of the (R)-(+)-tert-butylsulfinamide (66 mmol) in THF (350 ml) was added subsequently the ketone B1 (72.6 mmol) and titanium(IV)ethoxide (132 mmol) and the solution was stirred at reflux temperature for 5 h. The mixture was cooled to 22° C., treated with brine (400 ml), the suspension was stirred for 10 min and filtered over dicalite. The layers were separated, the aqueous layer was extracted with ethyl acetate, the combined organic layers were washed with water, dried and concentrated in vacuum. The residue was purified by chromatography on silica using cyclohexane/ethyl acetate to give the pure sulfinyl imine B2.

Intermediate B2A

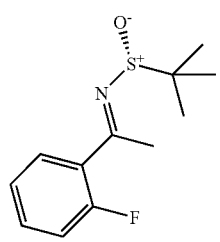 [SMILES: C/C(=N\[S@+]([O-])C(C)(C)C)c1ccccc1F]

Starting from 1-(2-fluoro-phenyl)-ethanone, the product (R)-2-methyl-propane-2-sulfinic acid [1-(2-fluoro-phenyl)-eth-(E)-ylidene]-amide was obtained as pale brown oil. MS (ISP): m/z=242.2 $[M+H]^+$.

Synthesis of the intermediate sulfinamide esters B3

General Procedure (Via Reformatsky Reaction)

In a dry apparatus a suspension of freshly activated zinc powder (1.63 g, 24.9 mmol) in dry THF (70 ml) was heated under inert atmosphere to reflux. A solution of the sulfinyl imine B2 (24.9 mmol) and the bromo-acetate (24.9 mmol) in dry THF (15 ml) was added dropwise over a period of 15 min and the suspension was heated to reflux for 5 h. The cooled mixture was partitioned between aqueous saturated NH$_4$Cl and ethyl acetate, the organic layer was dried and evaporated. The crude material was purified by flash chromatography using heptane/ethyl acetate to give the sulfinamide ester B3.

Intermediates B3A

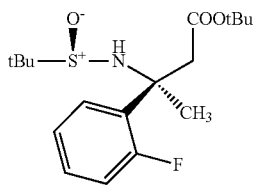

Starting from (R)-2-methyl-propane-2-sulfinic acid [1-(2-fluoro-phenyl)-eth-(E)-ylidene]-amide, the product (S)-3-(2-fluoro-phenyl)-(R)-3-(2-methyl-propane-2-sulfinylamino)-butyric acid tert-butyl ester was obtained as pale brown oil. MS (ISP): m/z=358.1 [M+H]$^+$.

Synthesis of the intermediate sulfinamide alcohols B4

General Procedure

A solution of the sulfinamide ester B3 (12.7 mmol) in dry THF (50 ml) was treated at 0° C. with lithium borohydride (25.3 mmol) and stirring was continued at 0° C. for 4 h. The reaction mixture was quenched by addition of acetic acid (2 ml) and water (50 ml), extracted with ethyl acetate and the organic layer was dried and evaporated. The residue was purified by chromatography on silica using a mixture of n-heptane and ethyl acetate to give the pure intermediate sulfinamide alcohol B4.

Intermediate B4A

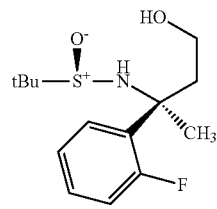 [SMILES: CC(C)(C)[S@+]([O-])N[C@@](C)(CCO)c1ccccc1F]

Starting from (S)-3-(2-fluoro-phenyl)-(R)-3-(2-methyl-propane-2-sulfinylamino)-butyric acid tert-butyl ester, the product (R)-2-methyl-propane-2-sulfinic acid [(S)-1-(2-fluoro-phenyl)-3-hydroxy-1-methyl-propyl]-amide was obtained as a yellow oil. MS (ISP): m/z=288.2 [M+H]$^+$.

Synthesis of the intermediate sulfinamide thioacetate B5

General Procedure

A solution of triphenylphosphine (4.73 g, 18.1 mmol) in 50 ml dry DCM at 0° C. under argon was treated with DCAD (6.63 g, 18.1 mmol) and the resulting reaction mixture stirred at 0° C. for 20 min. To the previous reaction mixture was added a solution of thioacetic acid (1.37 mg, 18.1 mmol) and the alcohol B4 (3.0 g, 9.03 mmol) in 10 ml dry DCM. The reaction mixture was stirred for 20 min at 0° C., was let to warm up to room temperature and stirred for 18 h at that temperature. The white precipitate, which formed during the course of the reaction, was filtered off. The filtrate was diluted with more DCM and extracted with a 1 M Na$_2$CO$_3$ aqueous solution. The organic layer was dried over sodium sulfate and evaporated down to dryness. The residue was purified by silica gel chromatography using a mixture of n-heptane and ethyl acetate to yield 3.2 g of sulfonamide thioacetate B5.

Intermediate B5A

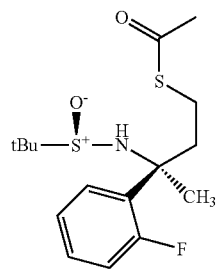 [SMILES: CC(=O)SCC[C@](C)(N[S@@+]([O-])C(C)(C)C)c1ccccc1F]

Starting from (R)-2-methyl-propane-2-sulfinic acid [(S)-1-(2-fluoro-phenyl)-3-hydroxy-1-methyl-propyl]-amide, the product thioacetic acid S—[(S)-3-(2-fluoro-phenyl)-(R)-3-(2-methyl-propane-2-sulfinylamino)-butyl]ester was obtained as a yellow oil. MS (ISP): m/z=346.2 [M+H]$^+$.

Synthesis of the intermediate sulfinamide thiol B6

General Procedure

A solution of sulfonamide thioacetate B5 (1.25 g, 3.62 mmol) in 25 ml MeOH was treated with K$_2$CO$_3$ (600 mg, 4.34 mmol), the reaction mixture was stirred at room temperature for a period of one hour. The reaction mixture was diluted with ethyl acetate and extracted with a saturated ammonium chloride solution. The organic layer was dried over sodium sulfate and evaporated down to dryness in vacuum. The residue was purified by silica gel chromatography using a mixture of n-heptane and ethyl acetate to give 810 mg of the sulfonamide thiol B6.

Intermediate B6A

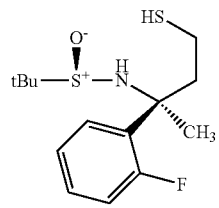 [SMILES: CC(C)(C)[S@+]([O-])N[C@@](C)(CCS)c1ccccc1F]

Starting from thioacetic acid S—[(S)-3-(2-fluoro-phenyl)-(R)-3-(2-methyl-propane-2-sulfinylamino)-butyl]ester, the product (R)-2-methyl-propane-2-sulfinic acid [(S)-1-(2-fluoro-phenyl)-3-mercapto-1-methyl-propyl]-amide was obtained as a yellow oil. MS (ISP): m/z=304.4 [M+H]⁺.

Synthesis of the intermediate sulfinamide ester B7

General Procedure

A solution of sulfinamide thiol B6 (1.8 g, 5.93 mmol) in 30 ml CH₃CN was treated with bromo ester (1.45 g, 7.41 mmol) and potassium carbonate (1.23 g, 8.9 mmol), the reaction mixture stirred at room temperature overnight. The reaction mixture was diluted with ethyl acetate and extracted with water, the organic layer was dried over sodium sulfate and evaporated down to dryness. The residue was purified by silica gel chromatography using a mixture of n-heptane and ethyl acetate to yield 1.68 g of the sulfinamide ester B7 as a colorless oil.

Intermediate B7A

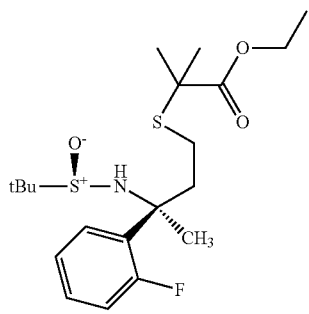 [SMILES: CCOC(=O)C(C)(C)SCC[C@](C)(N[S@@+]([O-])C(C)(C)C)c1ccccc1F]

Starting from (R)-2-methyl-propane-2-sulfinic acid [(S)-1-(2-fluoro-phenyl)-3-mercapto-1-methyl-propyl]-amide, the product (R)-2-[(S)-3-(2-fluoro-phenyl)-3-(2-methyl-propane-2-sulfinylamino)-butylsulfanyl]-2-methyl-propionic acid ethyl ester was obtained as a yellow oil. MS (ISP): m/z=418.4 [M+H]⁺.

Synthesis of the intermediate amino ester B8

General Procedure

A solution of sulfonamide ester B7 (1.47 g, 3.52 mmol) in 15 ml MeOH at 0° C. was treated with a 4 M hydrochloric acid solution in dioxane (4.4 ml, 17.6 mmol). The reaction mixture was stirred at room temperature for a period of one hour. The reaction mixture was diluted with ethyl acetate and extracted with a 2 M sodium carbonate aqueous solution. The organic layer was dried over sodium sulfate and evaporated down in vacuum to dryness. The residue was purified by silica gel chromatography using a mixture of n-heptane and ethyl acetate to give 1.05 g of the amino ester B8.

Intermediate B8A

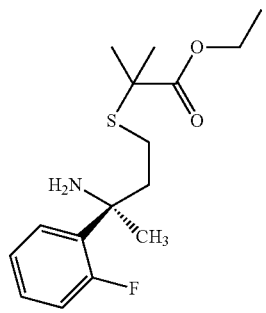 [SMILES: CCOC(=O)C(C)(C)SCC[C@](C)(N)c1ccccc1F]

Starting from (R)-2-[(S)-3-(2-fluoro-phenyl)-3-(2-methyl-propane-2-sulfinylamino)-butylsulfanyl]-2-methyl-propionic acid ethyl ester, the product 2-[(S)-3-amino-3-(2-fluoro-phenyl)-butylsulfanyl]-2-methyl-propionic acid ethyl ester was obtained as a yellow oil. MS (ISP): m/z=314.3 [M+H]⁺.

Synthesis of the intermediate lactam B9

General Procedure

A solution of amino ester B8 (1.05 g, 3.35 mmol) in 20 ml dry THF under argon was treated with bis[bis(trimethylsilyl)amino]tin(II) (1.49 ml, 3.85 mmol) at room temperature. The reaction mixture was stirred at 50° C. for a period of three hours and the reaction medium was poured into a mixture of water and ethyl acetate which was stirred for a period of 15 min. The resulting mixture was filtered over Celite® to remove the precipitate, the organic layer was collected, dried over sodium sulfate and evaporated down in vacuum to dryness. The residue was purified by silica gel chromatography using a mixture of n-heptane and ethyl acetate to give 480 mg of the lactam B9.

Intermediate B9A

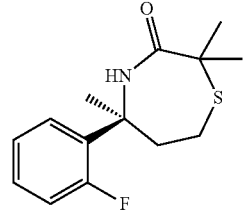 [SMILES: CC1(C)SCC[C@@](C)(c2ccccc2F)NC1=O]

Starting from 2-[(S)-3-amino-3-(2-fluoro-phenyl)-butylsulfanyl]-2-methyl-propionic acid ethyl ester, the product (S)-5-(2-fluoro-phenyl)-2,2,5-trimethyl-[1,4]thiazepan-3-one was obtained as a yellow oil. MS (ISP): m/z=268.1 [M+H]⁺.

Synthesis of the intermediate sulfone B10

General Procedure

A solution of lactam B9 (480 mg, 1.8 mmol) in 15 ml CH₂Cl₂ was treated with m-CPBA (929 mg, 3.77 mmol) at room temperature, the reaction mixture was stirred over a period of 14 hours at room temperature. The reaction mixture was diluted with dichloromethane and extracted with a 2 M sodium carbonate aqueous solution, the organic layer was dried over sodium sulfate and evaporated down in vacuum to dryness. The crude was purified by silica gel chromatography using a mixture of n-heptane and ethyl acetate to give 525 mg of the sulfone B10.

Intermediate B10A

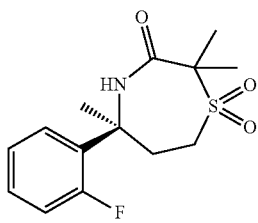 [SMILES: CC1(C)C(=O)N[C@](C)(c2ccccc2F)CCS1(=O)=O]

Starting from (S)-5-(2-fluoro-phenyl)-2,2,5-trimethyl-[1,4]thiazepan-3-one, the product (S)-5-(2-fluoro-phenyl)-2,2,5-trimethyl-1,1-dioxo-1$\lambda^6$-[1,4]thiazepan-3-one was obtained as colorless oil. MS (ISP): m/z=300.1 [M+H]$^+$.

Synthesis of the intermediate thioamide B11

General Procedure

A solution of sulfone B10 (525 mg, 1.75 mmol) in 10 ml dry THF was treated with Lawesson's reagent (922 mg, 2.28 mmol) at room temperature and the reaction mixture was stirred at 85° C. for a period of 2 hours. The reaction medium was diluted with ethyl acetate, extracted with water. The organic layer was dried over sodium sulfate and evaporated down in vacuum to dryness. The crude was purified by silica gel chromatography using a mixture of n-heptane and ethyl acetate to give 415 mg of the thioamide B11.

Intermediate B11A

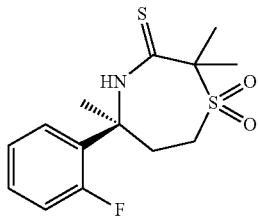 [SMILES: CC1(C)C(=S)N[C@](C)(c2ccccc2F)CCS1(=O)=O]

Starting from (S)-5-(2-fluoro-phenyl)-2,2,5-trimethyl-1,1-dioxo-1$\lambda^6$-[1,4]thiazepan-3-one, the product (S)-5-(2-fluoro-phenyl)-2,2,5-trimethyl-1,1-dioxo-2,5,6,7-tetrahydro-1H-1$\lambda^6$-[1,4]thiazepane-3-thione was obtained as a yellow oil. MS (ISP): m/z=316.1 [M+H]$^+$.

Synthesis of the intermediate 1,1-dioxo-[1,4]thiazepin B12

General Procedure

A solution of thioamide B11 (415 mg, 1.32 mmol) in 5 ml THF was treated with mercury(II) chloride (357 mg, 1.32 mmol) and a solution of ammonia 7 N in MeOH (752 μL, 5.26 mmol). The reaction mixture was stirred at 120° C. for 30 min in Micro-Wave cavity. The reaction medium was filtered on Celite to remove mercury salt which precipitated as black powder, the filtrate was diluted with ethyl acetate and extracted with a 2 M sodium carbonate aqueous solution. The organic layer was dried over sodium sulfate and evaporated down in vacuum to dryness. The crude was purified by silica gel chromatography using a mixture of dichloromethane and methanol to give the 1,1-dioxo-[1,4]thiazepin B12.

Intermediate B12A

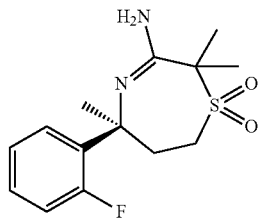 [SMILES: CC1(C)C(N)=N[C@](C)(c2ccccc2F)CCS1(=O)=O]

Starting from (S)-5-(2-fluoro-phenyl)-2,2,5-trimethyl-1,1-dioxo-2,5,6,7-tetrahydro-1H-1$\lambda^6$-[1,4]thiazepane-3-thione, the product (S)-5-(2-fluoro-phenyl)-2,2,5-trimethyl-1,1-dioxo-2,5,6,7-tetrahydro-1H-1$\lambda^6$-[1,4]thiazepin-3-ylamine was obtained as a colorless oil. MS (ISP): m/z=299.1 [M+H]$^+$.

Synthesis of the intermediate nitro B13

General Procedure 1,1-dioxo-[1,4]thiazepin B12 (300 mg, 1.01 mmol) was dissolved in H$_2$SO$_4$ 97% (ultrasound was necessary to complete dissolution, strong deep red color once completely dissolved) and the reaction mixture was cooled down to 0° C., followed by slow addition of nitric acid 100% (45 μL, 1.01 mmol). The resulting reaction mixture was stirred for a period of 15 minutes at 0° C. The reaction medium slowly poured into a mixture of ethyl acetate and water/ice, the resulting mixture was stirred for 10 min. The previous mixture was cooled down to 0° C. and potassium carbonate was added until pH reached 10-11. Two phases were separated and the organic layer was dried over sodium sulfate and evaporated down in vacuum to dryness. The crude was purified by silica gel chromatography using a mixture of dichloromethane and a solution of 10% triethylamine in methanol to give 185 mg of the nitro B13

Intermediate B13A

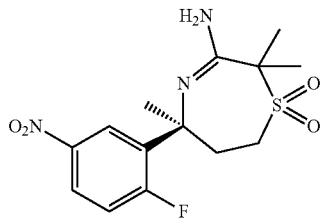 [SMILES: CC1(C)C(N)=N[C@](C)(c2cc([N+](=O)[O-])ccc2F)CCS1(=O)=O]

Starting from (S)-5-(2-fluoro-phenyl)-2,2,5-trimethyl-1,1-dioxo-2,5,6,7-tetrahydro-1H-1$\lambda^6$-[1,4]thiazepin-3-ylamine, the product (S)-5-(2-fluoro-5-nitro-phenyl)-2,2,5- trimethyl-1,1-dioxo-2,5,6,7-tetrahydro-1H-1λ⁶-[1,4]thiazepin-3-ylamine was obtained as a colorless oil. MS (ISP): m/z=344.1 [M+H]⁺.

Synthesis of the intermediate aniline B14

General Procedure

To a solution of nitrobenzene B13 (140 mg, 0.47 mmol) in 4.0 ml EtOH was added SnCl₂.2H₂O (321 mg, 1.42 mmol) (precipitate formed instantly which dissolved upon heating). Reaction stirred at 80° C. for 1.5 h and controlled by TLC Si—NH₂ (CH₂Cl₂/MeOH/NH₄OH 80:18:2) which showed complete conversion. Reaction mixture poured into an aqueous solution NaOH 1N, addition of ethyl acetate and the mixture was stirred for 10 min. Precipitate was filtered over Celite®, the two phases in the filtrate were separated. The organic phase was dried over Na₂SO₄, filtered and evaporated down to dryness. The residue was purified by chromatography on an amine-modified silica with a mixture of CH₂Cl₂ and MeOH to give the pure aniline B14.

Intermediate B14A

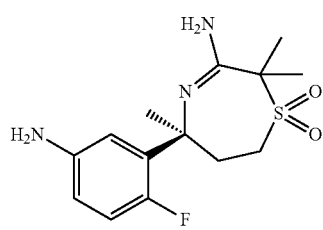

Starting from (S)-5-(2-fluoro-5-nitro-phenyl)-2,2,5-trimethyl-1,1-dioxo-2,5,6,7-tetrahydro-1H-1λ⁶-[1,4]thiazepin-3-ylamine, the product (S)-5-(5-amino-2-fluoro-phenyl)-2,2,5-trimethyl-1,1-dioxo-2,5,6,7-tetrahydro-1H-1λ⁶-[1,4]thiazepin-3-ylamine was obtained as colorless oil. MS (ISP): m/z=314.1 [M+H]⁺.

Intermediate B14B

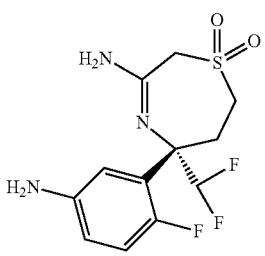 [SMILES: NC1=N[C@@](c2cc(N)ccc2F)(C(F)F)CCS(=O)(=O)C1]

A solution of {(RS)-5-[5-(benzhydrylidene-amino)-2-fluoro-phenyl]-5-difluoromethyl-1,1-dioxo-2,5,6,7-tetrahydro-1H-1λ⁶-[1,4]thiazepin-3-yl}-[bis-(4-methoxy-phenyl)-phenyl-methyl]-amine (207 mg, 263 μmol) in dichloromethane (10 ml) was treated with trifluoroacetic acid (1.01 ml, 13.1 mmol). The orange colored solution was stirred at room temperature for 1 hour. In order to cleave the intermediate benzophenonimine, hydrochloric acid (1M, 2.63 ml) and dioxane (10 ml) were added. The mixture was stirred at 23° C. for 4 hours. For the workup, the reaction mixture was poured into an aqueous solution of sodium carbonate (1 M) followed by the extraction with dichloromethane. The organic layer was washed with brine, dried over sodium sulfate and evaporated. The crude product was purified by chromatography on silica gel using a 110:10:1-mixture of dichloromethane, methanol and ammonium hydroxide as the eluent. The (RS)-5-(5-amino-2-fluoro-phenyl)-5-difluoromethyl-1,1-dioxo-2,5,6,7-tetrahydro-1H-1λ⁶-[1,4]thiazepin-3-ylamine (72 mg, 85% yield) was obtained as a light brown foam. MS (ISP): m/z=322.0 [M+H]⁺.

Synthesis of the intermediate amide B15

General Procedure

To a solution of the acid (0.16 mmol) in MeOH (1 ml) was added at 22° C. 4-(4,6-dimethoxy-1,3,5-triazin-2-yl)-4-methyl-morpholiniumchloride (0.19 mmol) and stirring was continued at 0° C. for 30 min. To the mixture was added a solution of the aniline B15 (0.15 mmol) in MeOH (2 ml) and stirring was continued at 0° C. for 2 h. The mixture was diluted with saturated aqueous Na₂CO₃, the MeOH was evaporated and the aqueous solution was extracted with ethyl acetate. The organic layer was dried, evaporated and the residue was purified by on silica gel chromatography using a mixture of dichloromethane and a solution of 3% triethylamine in methanol.

Intermediate C2A

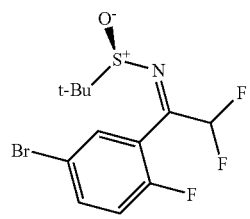 [SMILES: CC(C)(C)[S@@+]([O-])/N=C(\c1cc(Br)ccc1F)C(F)F]

In an analogous manner as described for the preparation of A2A, starting from 1-(5-bromo-2-fluorophenyl)-2,2-difluoroethanone (WO2011009943; CAS 1262858-97-8), the product (R)-2-methyl-propane-2-sulfinic acid [1-(5-bromo-2-fluoro-phenyl)-2,2-difluoro-eth-(E)-ylidene]-amide was obtained as a yellow oil. MS (EI): m/z=298 [M-t-Bu+H]⁺ and 300 [M-t-Bu+2+H]⁺.

Intermediate C3A

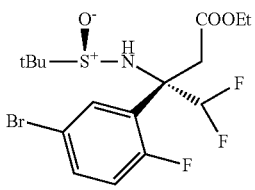 [SMILES: CCOC(=O)C[C@](N[S@@+]([O-])C(C)(C)C)(c1cc(Br)ccc1F)C(F)F]

In an analogous manner as described for the preparation of A3A, starting from (R)-2-methyl-propane-2-sulfinic acid [1-(5-bromo-2-fluoro-phenyl)-2,2-difluoro-eth-(E)-ylidene]-amide, the product (S)-3-(5-bromo-2-fluoro-phenyl)-4,4-difluoro-3-((R)-2-methyl-propane-2-sulfinylamino)-butyric acid ethyl ester (containing 30% of the undesired (R)-diastereomer, which was removed by preparative chiral HPLC on a Reprosil Chiral NR column with 5% EtOH in n-heptane as eluent) was obtained as a colorless oil. MS (ISP): m/z=444.0 [M+H]⁺and 446.0 [M+2+H]⁺.

Intermediate C4A

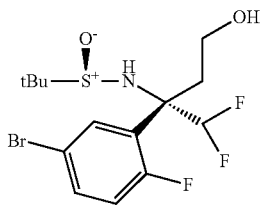 [SMILES: CC(C)(C)[S@+]([O-])N[C@@](CCO)(c1cc(Br)ccc1F)C(F)F]

In an analogous manner as described for the preparation of A4A, starting from (S)-3-(5-bromo-2-fluoro-phenyl)-4,4-difluoro-3-((R)-2-methyl-propane-2-sulfinylamino)-butyric acid ethyl ester, the product (R)-2-methyl-propane-2-sulfinic acid [(S)-1-(5-bromo-2-fluoro-phenyl)-1-difluoromethyl-3-hydroxy-propyl]-amide was obtained as a colorless oil. MS (ISN): m/z=399.9 [M−H]⁻ and 401.9 [M+2-H]⁻.

Intermediate C5A

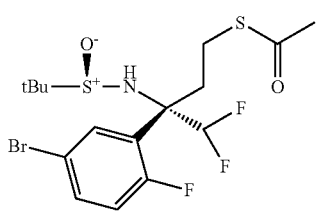 [SMILES: CC(=O)SCC[C@](N[S@@+]([O-])C(C)(C)C)(c1cc(Br)ccc1F)C(F)F]

In an analogous manner as described for the preparation of A5A, starting from (R)-2-methyl-propane-2-sulfinic acid [(S)-1-(5-bromo-2-fluoro-phenyl)-1-difluoromethyl-3-hydroxy-propyl]-amide, the product thioacetic acid 5-[(S)-3-(5-bromo-2-fluoro-phenyl)-4,4-difluoro-3-((R)-2-methyl-propane-2-sulfinylamino)-butyl]ester was obtained as a light yellow oil. MS (ISP): m/z=460.2 [M+H]⁺and 462.1 [M+2+H]⁺.

Intermediate C6A

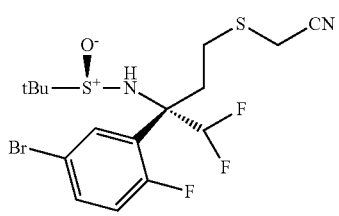 [SMILES: CC(C)(C)[S@+]([O-])N[C@@](CCSCC#N)(c1cc(Br)ccc1F)C(F)F]

In an analogous manner as described for the preparation of A6A, starting from thioacetic acid 5-[(S)-3-(5-bromo-2-fluoro-phenyl)-4,4-difluoro-3-((R)-2-methyl-propane-2-sulfinylamino)-butyl]ester, the product (R)-2-methyl-propane-2-sulfinic acid [(S)-1-(5-bromo-2-fluoro-phenyl)-3-cyanomethylsulfanyl-1-difluoromethyl-propyl]-amide was obtained as a colorless oil. MS (ISP): m/z=454.9 [M+H]⁺and 457.1 [M+2+H]⁺.

Intermediate C7A

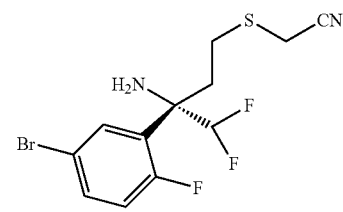 [SMILES: N#CCSCC[C@](N)(c1cc(Br)ccc1F)C(F)F]

In an analogous manner as described for the preparation of A7A, starting from (R)-2-methyl-propane-2-sulfinic acid [(S)-1-(5-bromo-2-fluoro-phenyl)-3-cyanomethylsulfanyl-1-difluoromethyl-propyl]-amide, the product [(S)-3-amino-3-(5-bromo-2-fluoro-phenyl)-4,4-difluoro-butylsulfanyl]-acetonitrile was obtained as a colorless oil. MS (ISP): m/z=352.9 [M+H]⁺and 354.9 [M+2+H]⁺.

Intermediate C8A

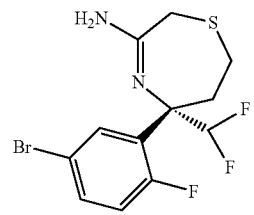 [SMILES: NC1=N[C@@](c2cc(Br)ccc2F)(C(F)F)CCSC1]

In an analogous manner as described for the preparation of A8A, starting from [(S)-3-amino-3-(5-bromo-2-fluoro-phenyl)-4,4-difluoro-butylsulfanyl]-acetonitrile, the product (S)-5-(5-bromo-2-fluoro-phenyl)-5-difluoromethyl-2,5,6,7-tetrahydro-[1,4]thiazepin-3-ylamine was obtained as a light yellow solid. MS (ISP): m/z=353.0 [M+H]⁺and 355.0 [M+2+H]⁺.

Intermediate C9A

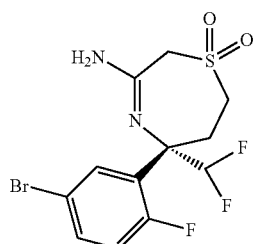

A solution of (S)-5-(5-bromo-2-fluoro-phenyl)-5-difluoromethyl-2,5,6,7-tetrahydro-[1,4]thiazepin-3-ylamine (364 mg, 1.03 mmol) in methanol (20 ml) was treated in two portions with potassium peroxymonosulfate (Oxone) (1.27 g, 2.06 mmol) at 23° C. The white suspension was stirred at 23° C. for 5 hours. For the workup, the reaction mixture was quenched at 0° C. under vigorous stirring with water (10 ml), then treated with a diluted solution of sodium hydrogensulfite, a saturated solution of sodium and with dichloromethane. The vigorous stirring was continued for 10 minutes. The organic layer was separated, washed with water, dried over sodium sulfate and evaporated to give a colorless oil. The crude product was purified by chromatography on silica gel using a gradient of dichloromethane and methanol 100:0 to 90:10 as the eluent. The (S)-5-(5-bromo-2-fluoro-phenyl)-5-difluoromethyl-1,1-dioxo-2,5,6,7-tetrahydro-1H-1λ⁶-[1,4]thiazepin-3-ylamine (322 mg, 81% yield) was obtained as a white solid. MS (ISP): m/z=384.9 [M+H]⁺and =386.9 [M+2+H]+.

Intermediate C10A

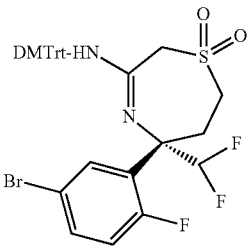

A solution of (S)-5-(5-bromo-2-fluoro-phenyl)-5-difluoromethyl-1,1-dioxo-2,5,6,7-tetrahydro-1H-1λ⁶-[1,4]thiazepin-3-ylamine (318 mg, 826 µmol) and triethylamine (167 mg, 1.65 mmol) in dichloromethane (15 ml) was treated at 0° C. with 4,4'-dimethoxytritylchloride (336 mg, 991 µmol). The green reaction mixture was stirred at room temperature for 6 hours. Thereafter, the reaction mixture was evaporated, and the crude product was purified by chromatography on silica gel using a gradient of heptane and ethyl acetate 100:0 to 50:50 as the eluent. The [bis-(4-methoxy-phenyl)-phenyl-methyl]-[(S)-5-(5-bromo-2-fluoro-phenyl)-5-difluoromethyl-1,1-dioxo-2,5,6,7-tetrahydro-1H-1λ⁶-[1,4]thiazepin-3-yl]-amine (365 mg, 63% yield) was obtained as a grey foam. MS (ISP): m/z=687.0 [M+H]⁺and 689.3 [M+2+H]⁺.

Intermediate C11A

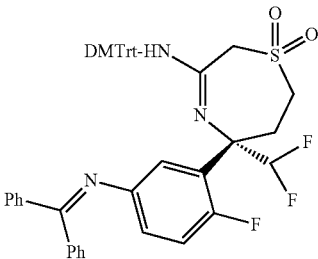

In a tube under an atmosphere of argon a solution of [bis-(4-methoxy-phenyl)-phenyl-methyl]-[(S)-5-(5-bromo-2-fluoro-phenyl)-5-difluoromethyl-1,1-dioxo-2,5,6,7-tetrahydro-1H-1λ⁶-[1,4]thiazepin-3-yl]-amine (356 mg, 518 µmol) in toluene (5 ml) was treated successively with sodium tert-butoxide (149 mg, 1.55 mmol), 2-di-tertbutylphosphino-2',4', 6'-triisopropylbiphenyl (33 mg, 77.7 µmol), tris(dibenzylideneacetone)dipalladium(0) chloroform adduct (26.8 mg, 26 µmol), and benzophenonimine (188 mg, 1.04 mmol). The tube was sealed and the mixture was heated at 105° C. under stirring for 4 hours. For the workup, the brown solution was extracted with ethyl acetate and water. The organic layer was washed with brine, dried over sodium sulfate and evaporated at reduced pressure. The crude product was purified by chromatography on silica gel using a gradient of heptane and ethyl acetate 100:0 to 50:50 as the eluent. The {(S)-5-[5-(benzhydrylidene-amino)-2-fluoro-phenyl]-5-difluoromethyl-1,1-dioxo-2,5,6,7-tetrahydro-1H-1λ⁶-[1,4]thiazepin-3-yl}-[bis-(4-methoxy-phenyl)-phenyl-methyl]-amine (207 mg, 51% yield) was obtained as a light yellow foam. MS (ISN): m/z=786.5 [M−H]⁻.

Intermediate D3

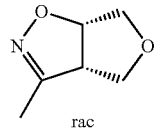

A solution of 2,5-dihydrofuran (5 g, 69.9 mmol) in ether (90 ml) was treated dropwise with a solution of nitroethane (5.46 g, 71.3 mmol) in ether (15 ml) at room temperature. Thereafter, triethylamine (70.7 mg, 699 µmol) was added followed by the dropwise addition of phenyl isocyanate (17.3 g, 143 mmol). The reaction mixture was stirred for 3 days at room temperature. For the workup, the white precipitate was filtered and washed with ether. The filtrate was evaporated and the crude product was purified by chromatography using a gradient of heptane and ethyl acetate=100:0 to 50:50 as the eluent. After a second chromatography the (3aS,6aS)-rel-3-methyl-3a,4,6,6a-tetrahydrofuro[3,4-d]isoxazole (58% yield) was obtained as a yellow oil.

Intermediate D5

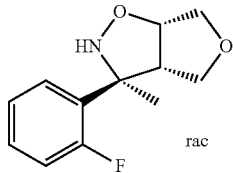 [SMILES: C[C@]1(c2ccccc2F)NO[C@@H]2COC[C@@H]21]

A solution of 1-bromo-2-fluorobenzene (31.1 g, 178 mmol) in a mixture of toluene (750 ml) and tetrahydrofuran (75 ml) was cooled to −100° C. Within 10 minutes a solution of n-butyllithium (1.6 M in hexane; 100 ml, 160 mmol) was added dropwise at a rate so that temperature could be maintained between −95 and −102° C. After 10 minutes stirring at −100° C. a mixture of (3aS,6aS)-rel-3-methyl-3a,4,6,6a-tetrahydrofuro[3,4-d]isoxazole (11.3 g, 88.9 mmol) and boron trifluoride diethyl etherate (25.2 g, 178 mmol) in a mixture of toluene (75 ml) and tetrahydrofuran (14 ml) was added within 3-5 minutes keeping the temperature below −94° C. The reaction mixture was stirred additional 10 minutes at −95 to −102° C. For the workup, a saturated solution of ammonium chloride (60 ml), water (100 ml) and ethyl acetate (200 ml) were added and the reaction mixture was left to warm to 0° C. The layers were separated and the aqueous layer was extracted once more with ethyl acetate. The combined organic layers were washed with brine, dried over sodium sulphate and evaporated at reduced pressure. The crude product was purified by chromatography using a gradient of heptane and ethyl acetate=100:0 to 0:100 as the eluent. The (3S,3aS,6aS)-rel-3-(2-fluoro-phenyl)-3-methyl-hexahydro-furo[3,4-d]isoxazole (17 g, 81% yield) was obtained as an off-white solid. MS (ISP): m/z=224.1 [M+H]$^+$.

Intermediate D6

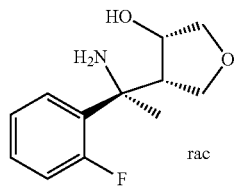 [SMILES: C[C@@](N)(c1ccccc1F)[C@H]1COC[C@H]1O]

A solution of (3S,3aS,6aS)-rel-3-(2-fluoro-phenyl)-3-methyl-hexahydro-furo[3,4-d]isoxazole (16.72 g, 72.9 mmol) in ethanol (300 ml) was treated with ammonium formate (36.8 g, 583 mmol) and palladium (5% on carbon; 7.76 g). The reaction mixture was stirred at room temperature for 18 hours, then filtered and the filtrate evaporated at reduced pressure. The crude product was triturated with diisopropyl ether (50 ml) and filtered. The filtrate was evaporated at reduced pressure and the (3S,4S)-4-[(S)-rel-1-amino-1-(2-fluoro-phenyl)-ethyl]-tetrahydro-furan-3-ol (8.69 g, 48% yield) was obtained as a thick colorless oil. MS (ISP): m/z=226.2 [M+H]$^+$. The solid material obtained after filtration, the rel-(3S,4S)-4-[(S)-1-amino-1-(2-fluoro-phenyl)-ethyl]-tetrahydro-furan-3-ol formate (8.21 g, 42% yield), was treated with a saturated solution of sodium hydrogencarbonate (100 ml) and with dichloromethane (100 ml) and stirred for 1 hour. The aqueous layer was separated and extracted with dichloromethane, then the combined organic layers were dried over sodium sulphate and evaporated. An additional amount of the rel-(3S,4S)-4-[(S)-1-amino-1-(2-fluoro-phenyl)-ethyl]-tetrahydro-furan-3-ol (5.6 g, 31% yield) was obtained as a thick colorless oil. MS (ISP): m/z=226.2 [M+H]$^+$.

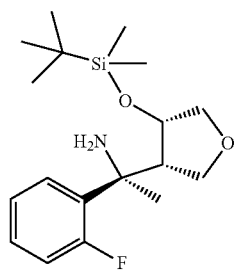 [SMILES: CC(C)(C)[Si](C)(C)O[C@@H]1COC[C@@H]1[C@](C)(N)c1ccccc1F]

Intermediate D7

Triethylamine (8.05 g, 79.6 mmol) was added to a solution of rel-(3S,4S)-4-((S)-1-amino-1-(2-fluorophenyl)ethyl)tetrahydrofuran-3-ol (5.6 g, 24.9 mmol) in dichloromethane (100 ml) at 0° C., then 4-dimethylaminopyridine (1.52 g, 12.4 mmol) followed by tert-butyldimethylchlorosilane (7.49 g, 49.7 mmol). The reaction mixture was stirred at room temperature overnight. For the workup, the reaction mixture was extracted with a saturated solution of sodium hydrogencarbonate and brine. The organic layer was dried over sodium sulphate and evaporated. The crude material was purified by flash chromatography on silica gel using a gradient of heptane and ethyl acetate=100:0 to 50:50 as the eluent. The rel-(S)-1-[(3S,4S)-4-(tert-butyl-dimethyl-silanyloxy)-tetrahydro-furan-3-yl]-1-(2-fluoro-phenyl)-ethylamine (8.13 g, 96% yield) was obtained as a colorless oil. MS (ISP): m/z=340.1 [M+H]$^+$.

Intermediate D9

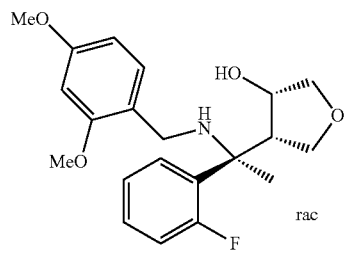

Under an atmosphere of argon, a solution of rel-(S)-1-[(3S,4S)-4-(tert-butyl-dimethyl-silanyloxy)-tetrahydro-furan-3-yl]-1-(2-fluoro-phenyl)-ethylamine (8.13 g, 23.9 mmol) in 1,2-dichloroethane (80 ml) was treated with 2,4-dimethoxy-benzaldehyde (3.98 g, 23.9 mmol), sodium triacetoxyborohydride (10.2 g, 47.9 mmol) and acetic acid (1.37 ml, 23.9 mmol). The reaction mixture was stirred overnight. In order to complete the reaction, 2,4-dimethoxybenzaldehyde (1.99 g, 12.0 mmol) and sodium triacetoxyborohydride (5.08 g, 23.9 mmol) were added and the mixture was stirred overnight. Thereafter, the reaction mixture was cooled to 0° C. and tetrabutylammonium fluoride trihydrate (7.56 g, 23.9 mmol) was added. The mixture was allowed to reach room temperature while stirring for 4 hours. In order to complete the reaction, tetrabutylammonium fluoride trihydrate (2.27 g, 7.18 mmol) was added again, and stirring continued for 4 days. For the workup, the reaction mixture was extracted twice with a mixture of a saturated solution of sodium hydrogencarbonate and dichloromethane. The combined organic layers were dried over sodium sulphate and evaporated. The residue was purified by flash chromatography on silica gel using a gradient of heptane and ethyl acetate=100:0 to 50:50 as the eluent. The rel-(3S,4S)-4-[(S)-1-(2,4-dimethoxy-benzylamino)-1-(2-fluoro-phenyl)-ethyl]-tetrahydro-furan-3-ol (6.8 g, 76% yield) was obtained as a colorless amorphous material.

Intermediate D10

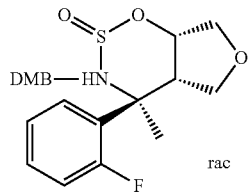

Under a dry atmosphere of argon, a solution of rel-(3S,4S)-4-[(S)-1-(2,4-dimethoxy-benzylamino)-1-(2-fluoro-phenyl)-ethyl]-tetrahydro-furan-3-ol (6.8 g, 18.1 mmol) in pyridine (7.32 ml, 90.5 mmol) and dichloromethane (120 ml) was cooled to −77° C. The colorless solution was treated dropwise with thionyl chloride (2.15 g, 18.1 mmol) over about 10 minutes while the temperature rose to −73° C. After removal of the cooling bath the reaction mixture was allowed to reach room temperature. For the workup, the reaction mixture was diluted with dichloromethane (150 ml) and washed consecutively with hydrochloric acid (1N) and a saturated solution of sodium hydrogencarbonate. The organic layer was dried over sodium sulphate and evaporated. The (3aS,7S,7aS)-rel-6-(2,4-dimethoxy-benzyl)-7-(2-fluoro-phenyl)-7-methyl-hexahydro-2,4-dioxa-5-thia-6-aza-indene 5-oxide (7.24 g, 95% yield) was obtained as a white solid. MS (ISP): m/z=422.0 [M+H]⁺.

Intermediate D11

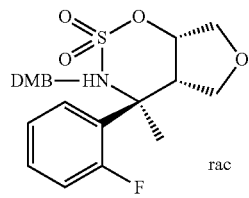

A solution of (3aS,7S,7aS)-rel-6-(2,4-dimethoxy-benzyl)-7-(2-fluoro-phenyl)-7-methyl-hexahydro-2,4-dioxa-5-thia-6-aza-indene 5-oxide (7.24 g, 17.2 mmol) and sodium periodate (4.04 g, 18.9 mmol) in a mixture of ethyl acetate (60 ml), acetonitrile (60 ml) and cold water (99.6 ml) was treated with ruthenium(III) chloride (35.6 mg, 172 μmol). The reaction mixture was stirred at 23° C. for 30 minutes. For the workup, the reaction mixture was extracted with a saturated solution of sodium hydrogencarbonate, the aqueous layer re-extracted with ethyl acetate, and the combined organic layers were dried over sodium sulphate and evaporated. The residue was purified by flash chromatography on silica gel using a gradient of heptane and ethyl acetate=100:0 to 0:100 as the eluent. The (3aS,7S,7aS)-rel-6-(2,4-dimethoxy-benzyl)-7-(2-fluoro-phenyl)-7-methyl-hexahydro-2,4-dioxa-5-thia-6-aza-indene 5,5-dioxide (4.1 g, 55% yield) was obtained as a light yellow solid. MS (ISP): m/z=460.2 [M+Na]⁺.

Intermediate D12

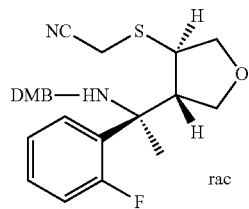

2-Mercaptoacetonitrile (1.03 g, 14.1 mmol) was added dropwise to a solution of (3aS,7S,7aS)-rel-6-(2,4-dimethoxy-benzyl)-7-(2-fluoro-phenyl)-7-methyl-hexahydro-2,4-dioxa-5-thia-6-aza-indene 5,5-dioxide (4.1 g, 9.37 mmol) and 1,1,3,3-tetramethylguanidine (1.62 g, 14.1 mmol) in N,N-dimethylformamide (55 ml) at room temperature. The reaction mixture was then stirred at 60° C. for 12 hours. For the workup, the solvent was evaporated at reduced pressure, and the residue was dissolved in dichloromethane (50 ml). After addition of sulfuric acid (20%; 50 ml, 185 mmol) and stirring overnight, the mixture was poured onto a saturated solution of sodium hydrogencarbonate followed by the extraction (2×) with dichloromethane. The combined organic layers were dried over sodium sulphate and evaporated. The residue was purified by flash chromatography on silica gel using a gradient of heptane and ethyl acetate=100:0 to 0:100 as the eluent. The {rel-(3R,4S)-4-[(S)-1-(2,4-dimethoxy-benzylamino)-1-(2-fluoro-phenyl)-ethyl]-tetrahydro-furan-3-ylsulfanyl}-acetonitrile (3.92 g, 97% yield) was obtained as a light brown oil. MS (ISP): m/z=431.2 [M+H]⁺.

Intermediate D13

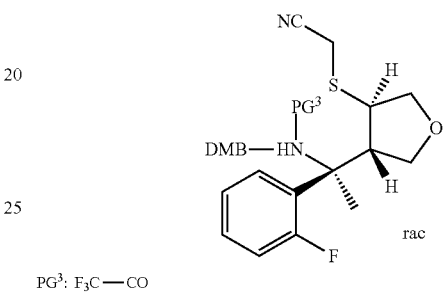

PG³: F₃C—CO

A solution of {rel-(3R,4S)-4-[(S)-1-(2,4-dimethoxy-benzylamino)-1-(2-fluoro-phenyl)-ethyl]-tetrahydro-furan-3-ylsulfanyl}-acetonitrile (1.75 g, 4.06 mmol) and triethylamine (1.13 ml, 8.13 mmol) in dichloromethane (8.75 ml) was treated dropwise at 0° C. with trifluoroacetic anhydride (1.28 g, 861 μl, 6.1 mmol). The reaction mixture was left to warm to room temperature and stirred overnight. For the workup, the reaction mixture was diluted with ethyl acetate and extracted with water. The organic layer was dried over sodium sulphate and evaporated at reduced pressure. The N-[rel-(S)-1-((3S,4R)-4-cyanomethylsulfanyl-tetrahydro-furan-3-yl)-1-(2-fluoro-phenyl)-ethyl]-N-(2,4-dimethoxy-benzyl)-2,2,2-trifluoro-acetamide (1.65 g, 77% yield) was obtained as a light yellow foam. MS (ISP): m/z=544.4 [M+NH₄]⁺.

Intermediate D14

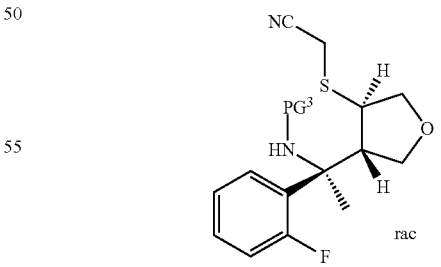

PG³: F₃C—CO

A solution of N-[rel-(S)-1-((3S,4R)-4-cyanomethylsulfanyl-tetrahydro-furan-3-yl)-1-(2-fluoro-phenyl)-ethyl]-N-(2,4-dimethoxy-benzyl)-2,2,2-trifluoro-acetamide (1.65 g, 3.13 mmol) in trifluoroacetic acid (14.5 ml, 188 mmol) was stirred at room temperature overnight. The reaction mixture was extracted with a mixture of a saturated solution of sodium hydrogencarbonate and ethyl acetate/tetrahydrofuran. The combined organic layers were dried over sodium sulphate and evaporated at reduced pressure. The crude N-[rel-(S)-1-((3S,4R)-4-cyanomethylsulfanyl-tetrahydro-furan-3-yl)-1-(2-fluoro-phenyl)-ethyl]-2,2,2-trifluoro-acetamide was obtained as a white solid and engaged in the following step without further purification. MS (ISP): m/z=375.3 [M+H]$^+$.

Intermediate D15

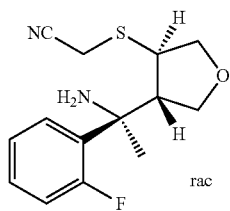 [SMILES: C[C@@](N)(c1ccccc1F)[C@H]1COC[C@@H]1SCC#N]

A solution of the crude N-[rel-(S)-1-((3S,4R)-4-cyanomethylsulfanyl-tetrahydro-furan-3-yl)-1-(2-fluoro-phenyl)-ethyl]-2,2,2-trifluoro-acetamide (2 g, 3.19 mmol) in ethanol (60 ml) was reacted with sodium borohydride (482 mg, 12.8 mmol) at 0° C. The reaction was left to warm to room temperature and stirred overnight. For the workup, the reaction mixture was extracted with a mixture of a saturated solution of sodium hydrogencarbonate and ethyl acetate. The combined organic layers were dried over sodium sulphate and evaporated at reduced pressure. The residue was purified by flash chromatography on silica gel using a gradient of heptane and ethyl acetate=100:0 to 0:100 as the eluent. The {rel-(3R,4S)-4-[(S)-1-amino-1-(2-fluoro-phenyl)-ethyl]-tetrahydro-furan-3-ylsulfanyl}-acetonitrile (510 mg, 57% yield) was obtained as a light yellow oil. MS (ISP): m/z=281.0 [M+H]$^+$.

Intermediate D16

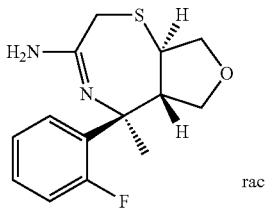 [SMILES: C[C@]1(c2ccccc2F)N=C(N)CS[C@H]2COC[C@@H]21]

A solution of the {rel-(3R,4S)-4-[(S)-1-amino-1-(2-fluoro-phenyl)-ethyl]-tetrahydro-furan-3-ylsulfanyl}-acetonitrile (460 mg, 1.64 mmol) in toluene (6 ml) was treated dropwise with trimethylaluminum (902 µl, 1.8 mmol) at room temperature. The reaction mixture was stirred at 60° C. for 2 hours, thereafter, extracted with a mixture of a saturated solution of sodium hydrogencarbonate and ethyl acetate. The combined organic layers were dried over sodium sulphate and evaporated at reduced pressure. The residue was purified by flash chromatography on silica gel using a mixture of ethyl acetate, methanol, ammonium hydroxide=100:10:1 as the eluent. The (3aR,8S,8aS)-rel-8-(2-fluoro-phenyl)-8-methyl-1,3,3a,5,8,8a-hexahydro-2-oxa-4-thia-7-aza-azulen-6-ylamine (200 mg, 43% yield) was obtained as a light yellow oil. MS (ISP): m/z=281.0 [M+H]$^+$.

Intermediate D17

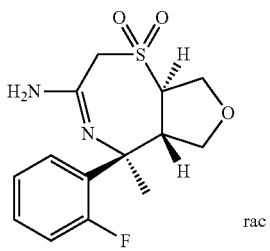 [SMILES: C[C@]1(c2ccccc2F)N=C(N)CS(=O)(=O)[C@H]2COC[C@@H]21]

3-chloroperbenzoic acid (251 mg, 1.02 mmol) was added at 0° C. to a solution of (3aR,8S,8aS)-rel-8-(2-fluoro-phenyl)-8-methyl-1,3,3a,5,8,8a-hexahydro-2-oxa-4-thia-7-aza-azulen-6-ylamine (130 mg, 464 µmol) in dichloromethane (20 ml). The reaction mixture was stirred at 0° C. for 2 hours, thereafter, extracted with a mixture of a saturated solution of sodium hydrogencarbonate and ethyl acetate. The combined organic layers were dried over sodium sulphate and evaporated at reduced pressure. The (3aR,8S,8aS)-rel-8-(2-fluoro-phenyl)-8-methyl-4,4-dioxo-3,3a,4,5,8,8a-hexahydro-1H-2-oxa-4λ$^6$-thia-7-aza-azulen-6-ylamine (110 mg, 76% yield) was obtained as a light brown solid. MS (ISP): m/z=281.0 [M+H]$^+$.

Intermediate D18

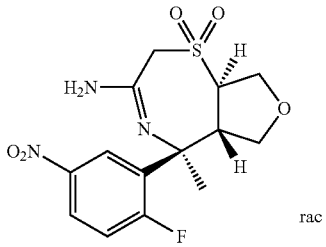

A solution of (3aR,8S,8aS)-rel-8-(2-fluoro-phenyl)-8-methyl-4,4-dioxo-3,3a,4,5,8,8a-hexahydro-1H-2-oxa-4λ$^6$-thia-7-aza-azulen-6-ylamine (110 mg, 176 µmol) in trifluoroacetic acid (1.33 g, 11.7 mmol) was cooled to 0-5° C. Sulfuric acid (149 mg, 81.2 µl, 1.52 mmol), then nitric acid (12.1 mg, 8.01 µl, 192 µmol) was added slowly. The reaction mixture was stirred at 0° C. for 1 hour. In order to complete the reaction, another equivalent of nitric acid (12.1 mg, 8.01 µl, 192 µmol) was added and stirring continued at 0° C. for 2 hours. For the workup, ice-water was added to the reaction mixture, and the resulting suspension was set to pH ~12 by addition of a solution of sodium hydroxide (32%). The mixture was extracted twice with ethyl acetate. The combined organic layers were washed with water, dried over sodium sulphate and evaporated. The crude (3aR,8S,8aS)-rel-8-(2-fluoro-5-nitro-phenyl)-8-methyl-4,4-dioxo-3,3a,4,5,8,8a-hexahydro-1H-2-oxa-4λ$^6$-thia-7-aza-azulen-6-ylamine was obtained as a brown solid and was engaged in the next step without purification. MS (ISP): m/z=358.3 [M+H]⁺.

Intermediate D19

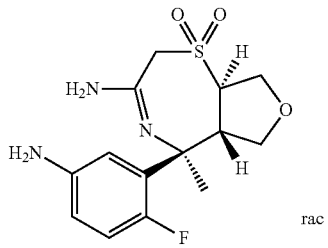 [SMILES: C[C@]1(c2cc([N+](=O)[O-])ccc2F)N=C(N)CS(=O)(=O)[C@H]2COC[C@@H]21]

The crude (3aR,8S,8aS)-rel-8-(2-fluoro-5-nitro-phenyl)-8-methyl-4,4-dioxo-3,3a,4,5,8,8a-hexahydro-1H-2-oxa-4$\lambda^6$-thia-7-aza-azulen-6-ylamine (73 mg, 204 µmol) was hydrogenated under atmospheric pressure at room temperature in ethanol (5 ml) using palladium on carbon (5%; 39 mg, 18.3 µmol) as the catalyst. After 3 hours the catalyst was filtered and the filtrate evaporated at reduced pressure. In order to complete the reaction, the residue was hydrogenated in a mixture of ethanol (5 ml) and tetrahydrofuran (5 ml) under the aforementioned conditions during 20 hours. Thereafter, the catalyst was filtered, and the filtrate was evaporated at reduced pressure. The crude (3aR,8S,8aS)-rel-8-(5-amino-2-fluoro-phenyl)-8-methyl-4,4-dioxo-3,3a,4,5,8,8a-hexahydro-1H-2-oxa-4$\lambda^6$-thia-7-aza-azulen-6-ylamine (70 mg) was obtained as brown semisolid material and was engaged in the next step without purification. MS (ISP): m/z=328.3 [M+H]⁺.

EXAMPLE 1

5-Chloro-pyridine-2-carboxylic acid [3-((S)-3-amino-5-methyl-2,5,6,7-tetrahydro-[1,4]thiazepin-5-yl)-4-fluoro-phenyl]-amide The compound was prepared using procedure for the synthesis of amide A9 from (S)-5-(5-amino-2-fluoro-phenyl)-5-methyl-2,5,6,7-tetrahydro-[1,4]thiazepin-3-ylamine (intermediate A8A). The title compound was obtained as a white solid. MS (ISP): m/z=393.3 [(M+H)⁺].

EXAMPLE 2

5-Fluoro-pyridine-2-carboxylic acid [3-((S)-3-amino-5-methyl-2,5,6,7-tetrahydro-[1,4]thiazepin-5-yl)-4-fluoro-phenyl]-amide The compound was prepared in an analogous manner as described for example 1 from (S)-5-(5-amino-2-fluoro-phenyl)-5-methyl-2,5,6,7-tetrahydro-[1,4]thiazepin-3-ylamine (intermediate A8A). The title compound was obtained as a white solid. MS (ISP): m/z=377.1 [(M+H)⁺].

EXAMPLE 3

5-Chloro-pyridine-2-carboxylic acid [3-((S)-3-amino-5-methyl-1,1-dioxo-2,5,6,7-tetrahydro-1H-1$\lambda^6$-[1,4]thiazepin-5-yl)-4-fluoro-phenyl]-amide The compound was prepared using the procedure for the synthesis of sulfone A10 from 5-chloro-pyridine-2-carboxylic acid [3-((S)-3-amino-5-methyl-2,5,6,7-tetrahydro-[1,4]thiazepin-5-yl)-4-fluoro-phenyl]-amide. The title compound was obtained as a white solid. MS (ISP): m/z=425.1 [(M+H)⁺].

EXAMPLE 4

5-Fluoro-pyridine-2-carboxylic acid [3-((S)-3-amino-5-methyl-1,1-dioxo-2,5,6,7-tetrahydro-1H-1$\lambda^6$-[1,4]thiazepin-5-yl)-4-fluoro-phenyl]amide The compound was prepared in an analogous manner as described for example 3 from 5-fluoro-pyridine-2-carboxylic acid [3-((S)-3-amino-5-methyl-2,5,6,7-tetrahydro-[1,4]thiazepin-5-yl)-4-fluoro-phenyl]-amide. The title compound was obtained as a white solid. MS (ISP): m/z=409.1 [(M+H)⁺].

EXAMPLE 5

5-Fluoro-pyridine-2-carboxylic acid [3-((S)-3-amino-2,5-dimethyl-2,5,6,7-tetrahydro-[1,4]thiazepin-5-yl)-4-fluoro-phenyl]-amide The compound was prepared in an analogous manner as described for example 1 from (S)-5-(5-amino-2-fluoro-phenyl)-2,5-dimethyl-2,5,6,7-tetrahydro-[1,4]thiazepin-3-ylamine (intermediate A8B). The title compound was obtained as a white solid. MS (ISP): m/z=391.1 [(M+H)⁺].

EXAMPLE 6

5-Chloro-pyridine-2-carboxylic acid [3-((S)-3-amino-2,5-dimethyl-2,5,6,7-tetrahydro-[1,4]thiazepin-5-yl)-4-fluoro-phenyl]-amide The compound was prepared in an analogous manner as described for example 1 from (S)-5-(5-amino-2-fluoro-phenyl)-2,5-dimethyl-2,5,6,7-tetrahydro-[1,4]thiazepin-3-ylamine (intermediate A8B). The title compound was obtained as a white solid. MS (ISP): m/z=407.0 [(M+H)⁺].

EXAMPLE 7

5-Fluoro-pyridine-2-carboxylic acid [3-((S)-3-amino-2,5-dimethyl-1,1-dioxo-2,5,6,7-tetrahydro-1H-1$\lambda^6$-[1,4]thiazepin-5-yl)-4-fluoro-phenyl]-amide The compound was prepared in an analogous manner as described for example 3 from 5-fluoro-pyridine-2-carboxylic acid [3-((S)-3-amino-2,5-dimethyl-2,5,6,7-tetrahydro-[1,4]thiazepin-5-yl)-4-fluoro-phenyl]-amide. The title compound was obtained as a white solid. MS (ISP): m/z=423.0 [(M+H)⁺].

EXAMPLE 8

5-Chloro-pyridine-2-carboxylic acid [3-((S)-3-amino-2,5-dimethyl-1,1-dioxo-2,5,6,7-tetrahydro-4H-1$\lambda^6$-[1,4]thiazepin-5-yl)-4-fluoro-phenyl]-amide The compound was prepared in an analogous manner as described for example 3 from 5-chloro-pyridine-2-carboxylic acid [3-((S)-3-amino-2,5-dimethyl-2,5,6,7-tetrahydro-[1,4]thiazepin-5-yl)-4-fluoro-phenyl]-amide. The title compound was obtained as a white solid. MS (ISP): m/z=439.1 [(M+H)⁺].

EXAMPLE 9

4-Chloro-2H-pyrazole-3-carboxylic acid [3-((S)-3-amino-2,5-dimethyl-1,1-dioxo-2,5,6,7-tetrahydro-1H-1$\lambda^6$-[1,4]thiazepin-5-yl)-4-fluoro-phenyl]-amide The compound was prepared in an analogous manner as described for example 3 from (S)-5-(5-amino-2-fluoro-phenyl)-2,5-dimethyl-2,5,6,7-tetrahydro-[1,4]thiazepin-3-ylamine (intermediate A9B). The title compound was obtained as a white solid. MS (ISP): m/z=428.0 [(M+H)$^+$].

EXAMPLE 10

5-Fluoro-pyridine-2-carboxylic acid [3-((S)-3-amino-2,2,5-trimethyl-1,1-dioxo-2,5,6,7-tetrahydro-1H-1$\lambda^6$-[1,4]thiazepin-5-yl)-4-fluoro-phenyl]-amide The compound was prepared using the procedure for the synthesis of the amide B15 from (S)-5-(5-amino-2-fluoro-phenyl)-2,2,5-trimethyl-1,1-dioxo-2,5,6,7-tetrahydro-1H-1$\lambda^6$-[1,4]thiazepin-3-ylamine (intermediate B14). The title compound was obtained as a white solid. MS (ISP): m/z=437.1 [(M+H)$^+$].

EXAMPLE 11

4-Chloro-2H-pyrazole-3-carboxylic acid [3-((S)-3-amino-2,2,5-trimethyl-1,1-dioxo-2,5,6,7-tetrahydro-1H-1$\lambda^6$-[1,4]thiazepin-5-yl)-4-fluoro-phenyl]-amide The compound was prepared in an analogous manner as described for example 10 from (S)-5-(5-amino-2-fluoro-phenyl)-2,2,5-trimethyl-1,1-dioxo-2,5,6,7-tetrahydro-1H-1$\lambda^6$-[1,4]thiazepin-3-ylamine (intermediate B14). The title compound was obtained as a white solid. MS (ISP): m/z=442.4 [(M+H)$^+$].

EXAMPLE 12

5-Cyano-pyridine-2-carboxylic acid [3-((S)-3-amino-2,2,5-trimethyl-1,1-dioxo-2,5,6,7-tetrahydro-1H-1$\lambda^6$-[1,4]thiazepin-5-yl)-4-fluoro-phenyl]-amide The compound was prepared in an analogous manner as described for example 10 from (S)-5-(5-amino-2-fluoro-phenyl)-2,2,5-trimethyl-1,1-dioxo-2,5,6,7-tetrahydro-1H-1$\lambda^6$-[1,4]thiazepin-3-ylamine (intermediate B14). The title compound was obtained as a light yellow oil. MS (ISP): m/z=444.3 [(M+H)$^+$].

EXAMPLE 13

5-Cyano-pyridine-2-carboxylic acid [3-((S)-3-amino-5-difluoromethyl-1,1-dioxo-2,5,6,7-tetrahydro-1H-1$\lambda^6$-[1,4]thiazepin-5-yl)-4-fluoro-phenyl]-amide The compound was prepared in an analogous manner as described for example 10 from (S)-5-(5-amino-2-fluoro-phenyl)-5-difluoromethyl-1,1-dioxo-2,5,6,7-tetrahydro-1H-1$\lambda^6$-[1,4]thiazepin-3-ylamine (intermediate B14B). The title compound was obtained as an off-white solid. MS (ISP): m/z=452.0 [(M+H)$^+$].

EXAMPLE 14

5-Cyano-pyridine-2-carboxylic acid [3-((3aR,8S,8aS)-rel-6-amino-8-methyl-4,4-dioxo-3,3a,4,5,8,8a-hexahydro-1H-2-oxa-4$\lambda^6$-thia-7-aza-azulen-8-yl)-4-fluoro-phenyl]-amide A solution of 5-cyanopyridine-2-carboxylic acid (15.8 mg, 107 μmol) in methanol (1 ml) was cooled to 0° C. After addition of 4-(4,6-dimethoxy-1,3,5-triazin-2-yl)-4-methyl-morpholiniumchloride (29.6 mg, 107 μmol) the mixture was stirred at 0° C. for 30 minutes. The crude (3aR,8S,8aS)-rel-8-(5-amino-2-fluoro-phenyl)-8-methyl-4,4-dioxo-3,3a,4,5,8,8a-hexahydro-1H-2-oxa-4$\lambda^6$-thia-7-aza-azulen-6-ylamine (70 mg, 107 μmol) was added, and the mixture left to warm to room temperature. After stirring for 21 hours, the light brown solution was decanted from the sticky solid formed and evaporated at reduced pressure. The residual amorphous material was purified by preparative HPLC using a gradient of water and methanol=95:5 to 0:100 (+0.05% formic acid) as the eluent. The 5-cyano-pyridine-2-carboxylic acid [3-((3aR,8S,8aS)-rel-6-amino-8-methyl-4,4-dioxo-3,3a,4,5,8,8a-hexahydro-1H-2-oxa-4$\lambda^6$-thia-7-aza-azulen-8-yl)-4-fluoro-phenyl]-amide (17 mg) was obtained as a light brown amorphous material. MS (ISP): m/z=458.4 [(M+H)$^+$].

The invention claimed is:
1. A compound of formula

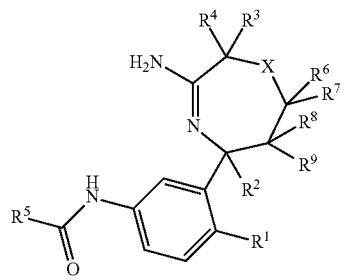

I wherein
$R^1$ is selected from the group consisting of
  hydrogen,
  halogen, and
  $C_{1-6}$-alkyl;
$R^2$ is selected from the group consisting of
  hydrogen,
  $C_{1-6}$-alkyl, and
  halogen-$C_{1-6}$-alkyl;
$R^3$ is selected from the group consisting of
  hydrogen and
  $C_{1-6}$-alkyl;
$R^4$ is selected from the group consisting of
  hydrogen and
  $C_{1-6}$-alkyl;
$R^5$ is heteroaryl unsubstituted or substituted by one or two substituents individually selected from the group consisting of
  $C_{1-6}$-alkyl,
  halogen, C$_{1-6}$-alkoxy, and
halogen-C$_{1-6}$-alkyl;
R$^6$ is hydrogen;
R$^7$ is hydrogen;
R$^8$ is hydrogen;
R$^9$ is hydrogen;
or R$^6$ and R$^8$ together form a 5-6 membered heterocyclyl; and
X is selected from the group consisting of
—S and
—SO$_2$;
or a pharmaceutically acceptable salt thereof.

2. The compound of claim 1, having formula I'

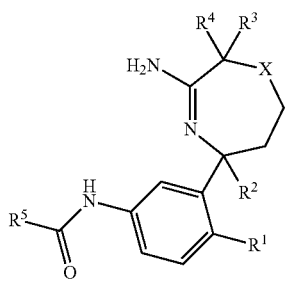

or a pharmaceutically acceptable salt thereof.

3. The compound of claim 2, having formula I'a

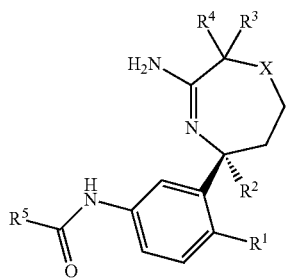

or a pharmaceutically acceptable salt thereof.

4. The compound of claim 1, wherein R$^1$ is halogen.
5. The compound of claim 4, wherein R$^1$ is F.
6. The compound of claim 1, wherein R$^2$ is C$_{1-6}$-alkyl.
7. The compound of claim 6, wherein R$^2$ is Me.
8. The compound of claim 1, wherein R$^3$ is C$_{1-6}$-alkyl.
9. The compound of claim 8, wherein R$^3$ is Me.
10. The compound of claim 1, wherein R$^4$ is C$_{1-6}$-alkyl.
11. The compound of claim 10, wherein R$^4$ is Me.
12. The compound of claim 1, wherein R$^4$ is hydrogen.
13. The compound of claim 1, wherein R$^5$ is heteroaryl substituted by one halogen selected from chloro and fluoro.
14. The compound of claim 1, wherein R$^5$ is selected from
chloro-pyridinyl,
fluoro-pyridinyl, and
2H-pyrazolyl.
15. The compound of claim 14, wherein R$^5$ is 5-chloro-pyridine-2-yl or 5-fluoro-pyridine-2-yl.
16. The compound of claim 1, wherein X is —S.
17. The compound of claim 1, wherein X is —SO$_2$.
18. The compound of claim 1, wherein R$^6$ and R$^8$ form together a 5-6 membered heterocyclyl.

19. The compound of claim 18, wherein R$^6$ and R$^8$ form together tetrahydrofuryl.
20. The compound of claim 1, selected from the group consisting of
5-Chloro-pyridine-2-carboxylic acid [3-((S)-3-amino-5-methyl-2,5,6,7-tetrahydro-[1,4]thiazepin-5-yl)-4-fluoro-phenyl]-amide,
4-Chloro-2H-pyrazole-3-carboxylic acid [3-((S)-3-amino-2,2,5-trimethyl-1,1-dioxo-2,5,6,7-tetrahydro-1H-1λ$^6$-[1,4]thiazepin-5-yl)-4-fluoro-phenyl]-amide,
4-Chloro-2H-pyrazole-3-carboxylic acid [3-((S)-3-amino-2,5-dimethyl-1,1-dioxo-2,5,6,7-tetrahydro-1H-1λ$^6$-[1,4]thiazepin-5-yl)-4-fluoro-phenyl]-amide,
5-Chloro-pyridine-2-carboxylic acid [3-((S)-3-amino-2,5-dimethyl-2,5,6,7-tetrahydro-[1,4]thiazepin-5-yl)-4-fluoro-phenyl]-amide,
5-Chloro-pyridine-2-carboxylic acid [3-((S)-3-amino-2,5-dimethyl-1,1-dioxo-2,5,6,7-tetrahydro-1H-1λ$^6$-[1,4]thiazepin-5-yl)-4-fluoro-phenyl]-amide,
5-Chloro-pyridine-2-carboxylic acid [3-((S)-3-amino-5-methyl-1,1-dioxo-2,5,6,7-tetrahydro-1H-1λ$^6$-[1,4]thiazepin-5-yl)-4-fluoro-phenyl]-amide,
5-Fluoro-pyridine-2-carboxylic acid [3-((S)-3-amino-2,2,5-trimethyl-1,1-dioxo-2,5,6,7-tetrahydro-1H-1λ$^6$-[1,4]thiazepin-5-yl)-4-fluoro-phenyl]-amide,
5-Fluoro-pyridine-2-carboxylic acid [3-((S)-3-amino-2,5-dimethyl-2,5,6,7-tetrahydro-[1,4]thiazepin-5-yl)-4-fluoro-phenyl]-amide,
5-Fluoro-pyridine-2-carboxylic acid [3-((S)-3-amino-2,5-dimethyl-1,1-dioxo-2,5,6,7-tetrahydro-1H-1λ$^6$-[1,4]thiazepin-5-yl)-4-fluoro-phenyl]-amide,
5-Fluoro-pyridine-2-carboxylic acid [3-((S)-3-amino-5-methyl-1,1-dioxo-2,5,6,7-tetrahydro-1H-1λ$^6$-[1,4]thiazepin-5-yl)-4-fluoro-phenyl]-amide and
5-Fluoro-pyridine-2-carboxylic acid [3-((S)-3-amino-5-methyl-2,5,6,7-tetrahydro-[1,4]thiazepin-5-yl)-4-fluoro-phenyl]-amide,
or a pharmaceutical acceptable salt thereof.

21. The compound of claim 1, selected from the group consisting of
5-Chloro-pyridine-2-carboxylic acid [3-((S)-3-amino-5-methyl-1,1-dioxo-2,5,6,7-tetrahydro-1H-1λ$^6$-[1,4]thiazepin-5-yl)-4-fluoro-phenyl]-amide,
5-Chloro-pyridine-2-carboxylic acid [3-((S)-3-amino-2,5-dimethyl-1,1-dioxo-2,5,6,7-tetrahydro-1H-1λ$^6$-[1,4]thiazepin-5-yl)-4-fluoro-phenyl]-amide, and
5-Fluoro-pyridine-2-carboxylic acid [3-((S)-3-amino-5-methyl-1,1-dioxo-2,5,6,7-tetrahydro-1H-1λ$^6$-[1,4]thiazepin-5-yl)-4-fluoro-phenyl]-amide.

22. A pharmaceutical composition comprising a therapeutically effective amount of a compound of formula I

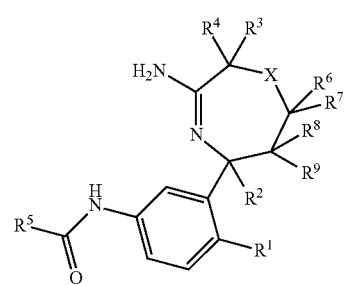

wherein
R$^1$ is selected from the group consisting of
hydrogen,
halogen, and
C$_{1-6}$-alkyl;
R$^2$ is selected from the group consisting of
hydrogen,
C$_{1-5}$-alkyl, and
halogen-C$_{1-6}$-alkyl;
R$^3$ is selected from the group consisting of
hydrogen and
C$_{1-6}$-alkyl;
R$^4$ is selected from the group consisting of
hydrogen and
C$_{1-6}$-alkyl;
R$^5$ is heteroaryl unsubstituted or substituted by one or two substituents individually selected from the group consisting of
C$_{1-6}$-alkyl
halogen,
C$_{1-6}$-alkoxy, and
halogen-C$_{1-6}$-alkyl;
R$^6$ is hydrogen;
R$^7$ is hydrogen;
R$^8$ is hydrogen;
R$^9$ is hydrogen;
or R$^6$ and R$^8$ together form a 5-6 membered heterocyclyl; and
X is selected from the group consisting of
—S and
—SO$_2$;
or a pharmaceutically acceptable salt thereof and a pharmaceutically acceptable carrier.

23. A compound, selected from the group consisting of
5-Cyano-pyridine-2-carboxylic acid [3-((S)-3-amino-2,2,5-trimethyl-1,1-dioxo-2,5,6,7-tetrahydro-1H-1λ6-[1,4]thiazepin-5-yl)-4-fluoro-phenyl]-amide,
5-Cyano-pyridine-2-carboxylic acid [3-((S)-3-amino-5-difluoromethyl-1,1-dioxo-2,5,6,7-tetrahydro-1H-1λ6-[1,4]thiazepin-5-yl)-4-fluoro-phenyl]-amide, and
5-Cyano-pyridine-2-carboxylic acid [3-((3aR,8S,8aS)-rel-6-amino-8-methyl-4,4-dioxo-3,3a,4,5,8,8a-hexahydro-1H-2-oxa-[[4λ6]]4λ$^6$-thia-7-aza-azulen-8-yl)-4-fluoro-phenyl]-amide,
or a pharmaceutical acceptable salt thereof.

* * * * *